(12) United States Patent
Lee et al.

(10) Patent No.: US 11,669,197 B2
(45) Date of Patent: Jun. 6, 2023

(54) ELECTRONIC DEVICE

(71) Applicant: Samsung Display Co., Ltd., Yongin-si (KR)

(72) Inventors: Soojung Lee, Suwon-si (KR); Yuna Kim, Seoul (KR); Chul Kim, Hwaseong-si (KR); Wonsang Park, Yongin-si (KR); Seungwook Chun, Daegu (KR); Boram Choi, Asan-si (KR); Yujin Choi, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 17/960,068

(22) Filed: Oct. 4, 2022

(65) Prior Publication Data

US 2023/0033511 A1 Feb. 2, 2023

Related U.S. Application Data

(62) Division of application No. 17/361,321, filed on Jun. 29, 2021, now Pat. No. 11,494,028.

(30) Foreign Application Priority Data

Oct. 6, 2020 (KR) .......................... 10-2020-0128805

(51) Int. Cl.
*G06F 3/00* (2006.01)
*G06F 3/041* (2006.01)
(Continued)

(52) U.S. Cl.
CPC ........ *G06F 3/04164* (2019.05); *G06F 3/0445* (2019.05); *H01L 27/323* (2013.01); *H01L 51/5237* (2013.01)

(58) Field of Classification Search
None
See application file for complete search history.

(56) References Cited

U.S. PATENT DOCUMENTS 10,034,616 B2 * 7/2018 Park ................... H03K 3/02337
10,433,759 B2 * 10/2019 Ahn ........................ G16H 40/67
(Continued)

FOREIGN PATENT DOCUMENTS

| KR | 10-1868688 | 6/2018 |
|----|------------|--------|
| KR | 10-2021-0018702 | 2/2021 |

OTHER PUBLICATIONS

Notice of Allowance dated Jul. 5, 2022, issued to U.S. Appl. No. 17/361,321.

(Continued)

*Primary Examiner* — Michael A Faragalla
(74) *Attorney, Agent, or Firm* — H.C. Park & Associates, PLC

(57) ABSTRACT

An electronic device includes: a display panel configured to display an image; an input sensor disposed on the display panel and including first electrodes and second electrodes electrically insulated from the first electrodes; and a sensor controller electrically connected to the input sensor, the sensor controller configured to drive the input sensor in a first driving mode or a second driving mode, wherein: in the first driving mode, the sensor controller is configured to measure a variation of capacitance between the first electrodes and the second electrodes to generate location information of an input, and in the second driving mode, the sensor controller is configured to use a first portion among the first electrodes as a transmission sensing electrode and to use a second portion among the first electrodes as a reception sensing electrode to analyze a body composition.

12 Claims, 21 Drawing Sheets

(51) Int. Cl.
    *H01L 51/52*     (2006.01)
    *H01L 27/32*     (2006.01)
    *G06F 3/044*     (2006.01)

(56) References Cited

U.S. PATENT DOCUMENTS

| | | |
|---|---|---|
| 2015/0018660 A1 | 1/2015 | Thomson et al. |
| 2016/0157749 A1 | 6/2016 | Bohorquez et al. |
| 2020/0253503 A1 | 8/2020 | Rutkove et al. |
| 2021/0043693 A1 | 2/2021 | Kim et al. |

OTHER PUBLICATIONS

Notice of Allowance dated Aug. 12, 2022, issued to U.S. Appl. No. 17/361,321.

* cited by examiner

ELECTRONIC DEVICE

CROSS-REFERENCE TO RELATED APPLICATIONS

This application is a Division of U.S. patent application Ser. No. 17/361,321, filed on Jun. 29, 2021, which claims priority from and the benefit of Korean Patent Application No. 10-2020-0128805, filed on Oct. 6, 2020, which is hereby incorporated by reference for all purposes as if fully set forth herein.

BACKGROUND

Field

Embodiments of the invention relate generally to an electronic device and more specifically, to an electronic device including an input sensor.

Discussion of the Background

Multimedia electronic devices, such as televisions, mobile phones, tablet computers, navigation units, and game units, include a display device for displaying images.

The electronic devices include an input sensor using a touch-based input method to provide users with easily and intuitively input information or commands in addition to the usual input methods, such as a button, a keyboard, a mouse, etc.

The above information disclosed in this Background section is only for understanding of the background of the inventive concepts, and, therefore, it may contain information that does not constitute prior art.

SUMMARY

Applicant realized that input sensors for electronic devices are generally used to obtain location information of inputs generated by users, and the usages of the input sensors are limited thereto.

Electronic devices with input sensors constructed according to the principles of the invention are capable of obtaining information of a body composition of the users as well as the location information of the inputs generated by the users.

According to an aspect of the invention, an electronic device includes: a display panel configured to display an image; an input sensor disposed on the display panel and including first electrodes and second electrodes electrically insulated from the first electrodes; and a sensor controller electrically connected to the input sensor, the sensor controller configured to drive the input sensor in a first driving mode or a second driving mode, wherein: in the first driving mode, the sensor controller is configured to measure a variation of capacitance between the first electrodes and the second electrodes to generate location information of an input, and in the second driving mode, the sensor controller is configured to use a first portion among the first electrodes as a transmission sensing electrode and to use a second portion among the first electrodes as a reception sensing electrode to analyze a body composition.

In the first driving mode, the first electrodes may be configured to receive transmission signals from the sensor controller, the second electrodes are configured to transmit reception signals to the sensor controller, and in the second driving mode, a first group among the first electrodes may be used as the transmission sensing electrode to receive transmission sensing signals from the sensor controller, and a second group among the first electrodes may be used as the reception sensing electrode to transmit reception sensing signals to the sensor controller.

The first group among the first electrodes may be disposed to be spaced apart from the second group among the first electrodes.

In the second driving mode, a third portion among the first electrodes may not be used as the transmission sensing electrode or the reception sensing electrode, and may be disposed between the transmission sensing electrode and the reception sensing electrode.

The third portion among the first electrodes may be defined as a peripheral electrode, and the peripheral electrode may be configured to receive a ground voltage in the second driving mode.

The third portion among the first electrodes may be defined as a peripheral electrode, and the peripheral electrode may be in a floating state in the second driving mode.

The first group among the first electrodes may include k first electrodes, the second group among the first electrodes may include j first electrodes, wherein n, k, and j may be natural numbers, and each of k and the j may be greater than 1 and smaller than n/2.

The natural number k may be equal to j.

The k first electrodes of the first group among the first electrodes may substantially simultaneously receive the transmission sensing signals from the sensor controller.

The k first electrodes of the first group among the first electrodes may sequentially receive the transmission sensing signals from the sensor controller.

The first electrodes may include transmission electrodes, and the second electrodes may include reception electrodes, and wherein: the transmission electrodes may extend in a first direction, and may be arranged in a second direction intersecting the first direction, and the reception electrodes may extend in the second direction, and may be arranged in the first direction.

The transmission sensing electrode may be disposed to be spaced apart from the reception sensing electrode in the second direction.

The first electrodes may include reception electrodes, and the second electrodes may include transmission electrodes, and wherein: the reception electrodes may extend in a second direction, and may be arranged in a first direction intersecting the second direction, and the transmission electrodes may extend in the first direction, and are arranged in the second direction.

The transmission sensing electrode may be disposed to be spaced apart from the reception sensing electrode in the first direction.

The display panel may include: a display element layer including a light emitting element; and an encapsulation layer disposed on the display element layer.

The input sensor may be disposed directly on the encapsulation layer.

The electronic device may further include an adhesive film disposed between the display panel and the input sensor.

According to another aspect of the invention, an electronic device includes: a display panel configured to display an image; an input sensor disposed on the display panel and including first electrodes and second electrodes electrically insulated from the first electrodes; and a sensor controller electrically connected to the input sensor, the sensor controller configured to drive the input sensor in a first driving mode or a second driving mode, wherein: in the first driving mode, the sensor controller is configured to measure a variation of capacitance between the first electrodes and the second electrodes to generate location information of an input, and in the second driving mode, the sensor controller is configured to operate in a first mode or in a second mode, and wherein: in the first mode of the second driving mode, the sensor controller is configured to analyze a body composition based on a variation of capacitance between a first group of the first electrodes and a second group of the first electrodes, and in the second mode of the second driving mode, the sensor controller is configured to analyze the body composition based on a variation of capacitance between a first group of the second electrodes and a second group of the second electrodes.

In the first driving mode, the first electrodes may be configured to receive transmission signals from the sensor controller, and the second electrodes may be configured to transmit reception signals to the sensor controller, in the first mode of the second driving mode, the first group among the first electrodes may be configured to receive transmission sensing signals from the sensor controller, the second group among the first electrodes may be configured to transmit reception sensing signals to the sensor controller, and in the second mode of the second driving mode, the first group among the second electrodes may be configured to receive the transmission sensing signals from the sensor controller, and the second group among the second electrodes may be configured to transmit the reception sensing signals to the sensor controller.

The first electrodes may extend in a first direction and may be arranged in a second direction, and the second electrodes may extend in the second direction and may be arranged in the first direction.

The first group of the first electrodes may be disposed to be spaced apart from the second group of the first electrodes in the second direction, and the first group of the second electrodes may be disposed to be spaced apart from the second group of the second electrodes in the first direction.

The display panel may include: a display element layer including a light emitting element; and an encapsulation layer disposed on the display element layer, and wherein the input sensor is disposed directly on the encapsulation layer.

According to another aspect of the invention, an electronic device includes: a display panel configured to display an image; an input sensor disposed on the display panel and including first electrodes, second electrodes electrically insulated from the first electrodes, and dummy electrodes electrically insulated from the first electrodes and the second electrodes; and a sensor controller electrically connected to the input sensor, the sensor controller configured to drive the input sensor in a first driving mode or a second driving mode, wherein: in the first driving mode, the sensor controller is configured to measure a variation of capacitance between the first electrodes and the second electrodes to generate location information of an input, and in the second driving mode, the sensor controller is configured to use a first group among the dummy electrodes as a transmission sensing electrode and to use a second group among the dummy electrodes as a reception sensing electrode to analyze a body composition.

In the first driving mode, the dummy electrodes may be in a floating state, in the second driving mode, the first group among the dummy electrodes may be configured to receive transmission sensing signals from the sensor controller, and in the second driving mode, the second group among the dummy electrodes may be configured to transmit reception sensing signals to the sensor controller.

Each of the first electrodes and the second electrodes may include a sensing part through which a center portion may be opened, and each of the dummy electrodes may be disposed to overlap the center portion of the sensing part.

The dummy electrodes of the first group among the dummy electrodes may be electrically connected to each other, and the dummy electrodes of the second group among the dummy electrodes may be electrically connected to each other.

The input sensor may further include: a first dummy connection part electrically connecting the dummy electrodes of the first group; and a second dummy connection part electrically connecting the dummy electrodes of the second group.

According to the above, the electronic device may analyze the body composition of the user using the input sensor that senses the input by the user. Accordingly, a field to which the electronic device is applied is expanded.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

Figure 1A:
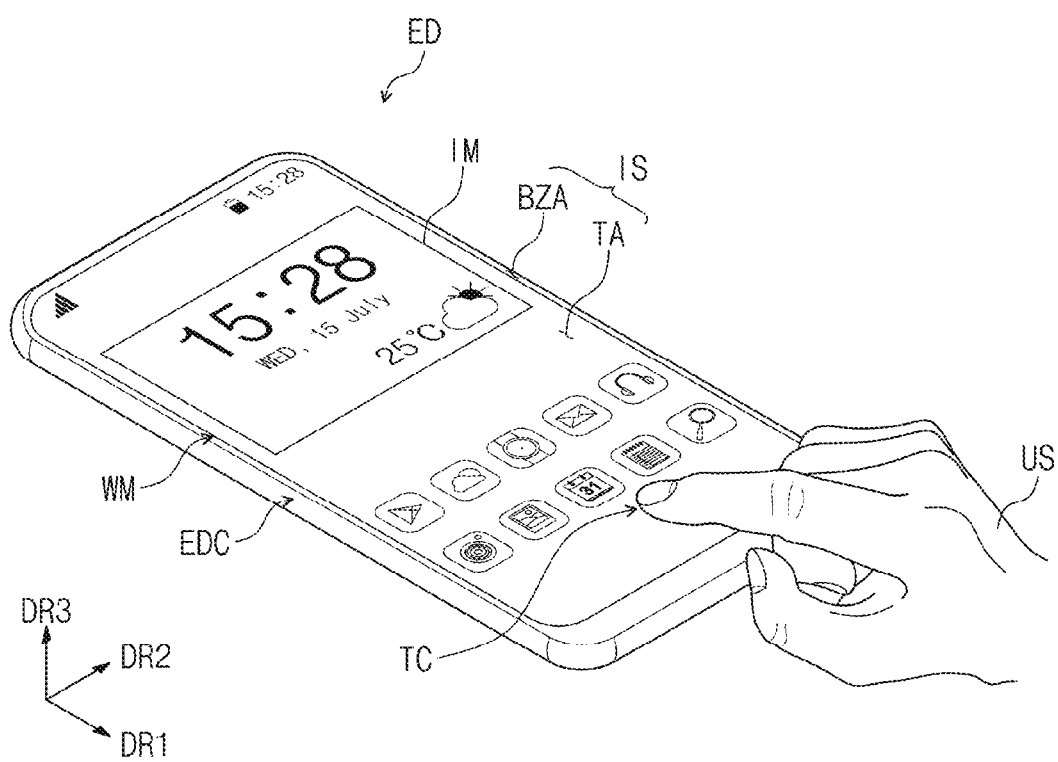
FIG. 1A is a perspective view of an embodiment of an electronic device constructed according to the principles of the invention.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some exemplary embodiments are described and illustrated in the accompanying drawings in terms of functional blocks, units, and/or modules, such as the sensor controller. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Hereinafter, embodiments will be explained in detail with reference to the accompanying drawings.

Figure 1B:
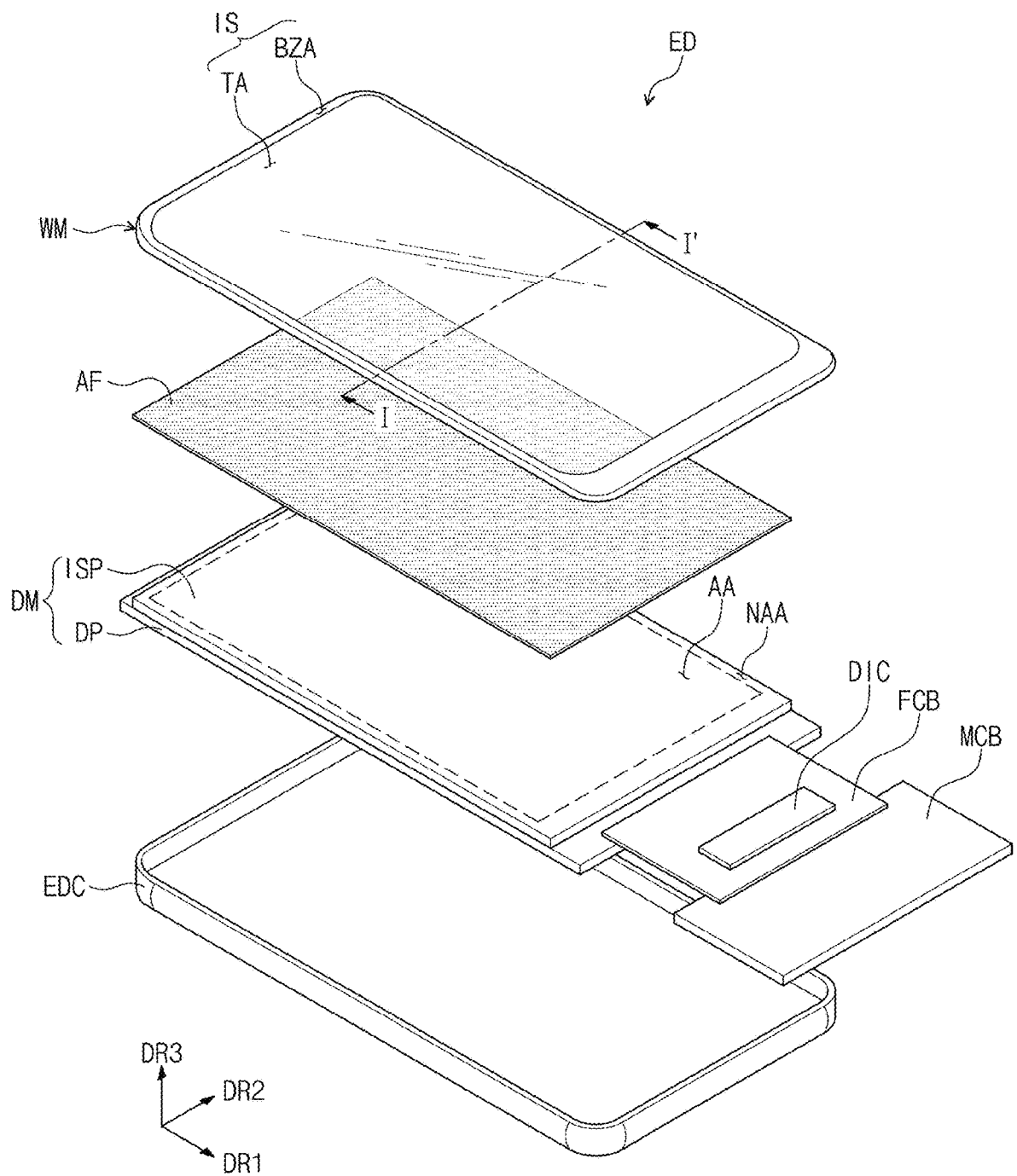
FIG. 1B is an exploded perspective view of the electronic device of FIG. 1A.
Figure 1C:
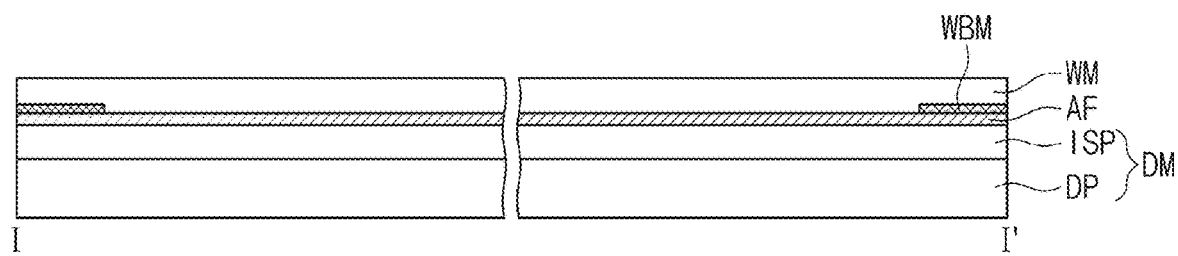
FIGS. 1C and 1D are cross-sectional views taken along a line I-I' shown in FIG. 1B illustrating embodiments of the electronic device.
Figure 1D:
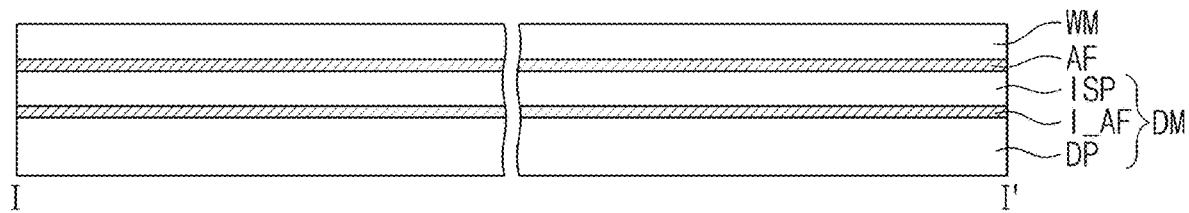

FIG. 1A is a perspective view showing an electronic device ED according to an embodiment, FIG. 1B is an exploded perspective view showing the electronic device ED according to an embodiment, and FIGS. 1C and 1D are cross-sectional views showing the electronic device ED taken along a line I-I' shown in FIG. 1B.

Referring to FIGS. 1A, 1B, and 1C, the electronic device ED may be activated in response to electrical signals. The electronic device ED may be applied to various electronic devices. For example, the electronic device ED may be applied to electronic devices, such as a smart watch, a tablet computer, a notebook computer, a computer, or a smart television.

The electronic device ED may display an image IM toward a third direction DR3 through a display surface IS substantially parallel to each of a first direction DR1 and a second direction DR2. The display surface IS through which the image IM is displayed may correspond to a front surface of the electronic device ED. The image IM may include a still image as well as a video image.

In an embodiment, front (e.g., upper) and rear (e.g., lower) surfaces of each member are defined with respect to a direction in which the image IM is displayed. The front and rear surfaces are opposite to each other in the third direction DR3, and a normal line direction of each of the front and rear surfaces is substantially parallel to the third direction DR3.

A distance in the third direction DR3 between the front surface and the rear surface may correspond to a thickness in the third direction DR3 of the electronic device ED. However, directions indicated by the first, second, and third directions DR1, DR2, and DR3 are relative to each other, and thus, the directions indicated by the first, second, and third directions DR1, DR2, and DR3 may be changed to other directions.

The electronic device ED may sense an external input TC applied thereto from the outside. The external input TC may include inputs of various forms provided from the outside of the electronic device ED. The external input TC may be one of various forms of external inputs, such as a portion of a user's body, light, heat, or pressure, or a combination thereof. In an embodiment, a touch input generated by a hand of the user US and applied to the front surface will be described as a representative example of the external input TC. However, embodiments are not limited thereto. For example, the external input TC may be provided in various forms.

The front surface of the electronic device ED may be divided into a transmission area TA and a bezel area BZA. The image IM may be displayed through the transmission area TA. The user may view the image IM through the transmission area TA. In an embodiment, the transmission area TA may have a quadrangular shape with rounded vertices. However, this is merely exemplary, and the transmission area TA may have a variety of shapes and should not be particularly limited thereto.

The bezel area BZA may be adjacent to the transmission area TA. The bezel area BZA may have a predetermined color. The bezel area BZA may surround the transmission area TA. Accordingly, the shape of the transmission area TA may be defined by the bezel area BZA, however, this is merely exemplary. For example, the bezel area BZA may be disposed adjacent to only one side of the transmission area TA or may be omitted. The electronic device ED according to an embodiment may be implemented in various forms.

As shown in FIG. 1B, the electronic device ED may include a display module DM and a window WM disposed on the display module DM. The display module DM may include a display panel DP and an input sensor ISP.

The display panel DP according to an embodiment may be a light-emitting type display panel. However, embodiments are not limited thereto. For instance, the display panel DP may be an organic light emitting display panel or a quantum dot light emitting display panel. A light emitting layer of the organic light emitting display panel may include an organic light emitting material. A light emitting layer of the quantum dot light emitting display panel may include a quantum dot or a quantum rod. Hereinafter, the organic light emitting display panel will be described as a representative example of the display panel DP.

Referring to FIG. 1C, the input sensor ISP may be disposed directly on the display panel DP. According to an embodiment, the input sensor ISP may be formed on the display panel DP through successive processes. For example, when the input sensor ISP is disposed directly on the display panel DP, an adhesive film may not be disposed between the input sensor ISP and the display panel DP. Alternatively, referring to FIG. 1D, an inner is adhesive film I_AF may be disposed between the input sensor ISP and the display panel DP. In this case, the input sensor ISP may not be manufactured through the successive processes with the display panel DP, and the input sensor ISP may be fixed to an upper surface of the display panel DP by the inner adhesive film I_AF after the input sensor ISP is manufactured through a separate process.

The display panel DP may generate the image, and the input sensor ISP may obtain location information of the external input, e.g., coordinate information.

The window WM may include a transparent material through which the image transmits. For example, the window WM may include glass, sapphire, or plastic. The window WM is shown in a single layer. However, embodiments are not limited thereto or thereby. For example, the window WM may include plural layers. Further, the bezel area BZA of the electronic device ED may be obtained by printing a material having the predetermined color on an area of the window WM. As an example, the window WM may include a light blocking pattern WBM to define the bezel area BZA. The light blocking pattern WBM may be a colored organic layer and may be formed by a coating method.

The window WM may be coupled to the display module DM by an adhesive film AF. As an example, the adhesive film AF may include an optically clear adhesive film (OCA). However, embodiments are not limited thereto or thereby. For example, the adhesive film AF may include a conventional adhesive. Further, the adhesive film AF may include an optically clear resin (OCR) or a pressure sensitive adhesive film (PSA).

An anti-reflective layer may be further disposed between the window WM and the display module DM. The anti-reflective layer may reduce a reflectance of an external light incident thereto from the above of the window WM. The anti-reflective layer according to an embodiment may include a retarder and a polarizer. The retarder may be a film type or liquid crystal coating type and may include a $\lambda/2$ retarder and/or a $\lambda/4$ retarder. The polarizer may be a film type or liquid crystal coating type. The film type polarizer may include a stretching type synthetic resin film, and the liquid crystal coating type polarizer may include liquid crystals aligned in a predetermined alignment. The retarder and the polarizer may be implemented as one polarizing film.

As another example, the anti-reflective layer may include color filters disposed directly on the input sensor ISP or the display panel DP.

The display module DM may display the image in response to electrical signals and may transmit or receive information of the external input. The display module DM may include an active area AA and a peripheral area NAA, which are defined therein. The active area AA may be defined as an area that emits the image provided from the display module DM.

The peripheral area NAA may be adjacent to the active area AA. For example, the peripheral area NAA may surround the active area AA. However, this is merely exemplary, and the peripheral area NAA may be defined in various shapes. According to an embodiment, the active area AA of the display module DM may correspond to at least a portion of the transmission area TA.

The display module DM may further include a main circuit board MCB, a flexible circuit film FCB, and a driving chip DIC. The main circuit board MCB may be connected to the flexible circuit film FCB and may be electrically connected to the display panel DP. The main circuit board MCB may include a plurality of driving elements. The driving elements may include a circuit unit to drive the display panel DP. The flexible circuit film FCB may be connected to the display panel DP to electrically connect the display panel DP to the main circuit board MCB. The driving chip DIC may be mounted on the flexible circuit film FCB.

The driving chip DIC may include driving elements, for example, a data driving circuit, to drive a pixel of the display panel DP. According to an embodiment, one flexible circuit film FCB is shown, however, the number of the flexible circuit films should not be limited to one. The flexible circuit film FCB may be provided in plural and may be connected to the display panel DP. FIG. 1B shows a structure in which the driving chip DIC is mounted on the flexible circuit film FCB. However, embodiments are not limited thereto or thereby. For example, the driving chip DIC may be mounted directly on the display panel DP. In this case, a portion of the display panel DP, on which the driving chip DIC is mounted, may be bent and may be disposed on a rear surface of the display module DM.

The input sensor ISP may be electrically connected to the main circuit board MCB via the flexible circuit film FCB. However, embodiments are not limited thereto or thereby. For example, the display module DM may further include a separate flexible circuit film to electrically connect the input sensor ISP to the main circuit board MCB.

The electronic device ED may further include an external case EDC that accommodates the display module DM. The external case EDC may be coupled to the window WM to define an exterior of the electronic device ED. The external case EDC may absorb impacts applied thereto from the outside and may prevent foreign substance and moisture from entering the display module DM, thereby protecting components accommodated in the external case EDC. Further, as an example, the external case EDC may be provided in a form in which a plurality of accommodation members is combined.

The electronic device ED according to an embodiment may further include an electronic module that includes various functional modules to operate the display module DM, a power supply module that supplies a power required for overall operation of the electronic device ED, and a bracket coupled to the display module DM and/or the external case EDC to divide an inner space of the electronic device ED.

Figure 2A:
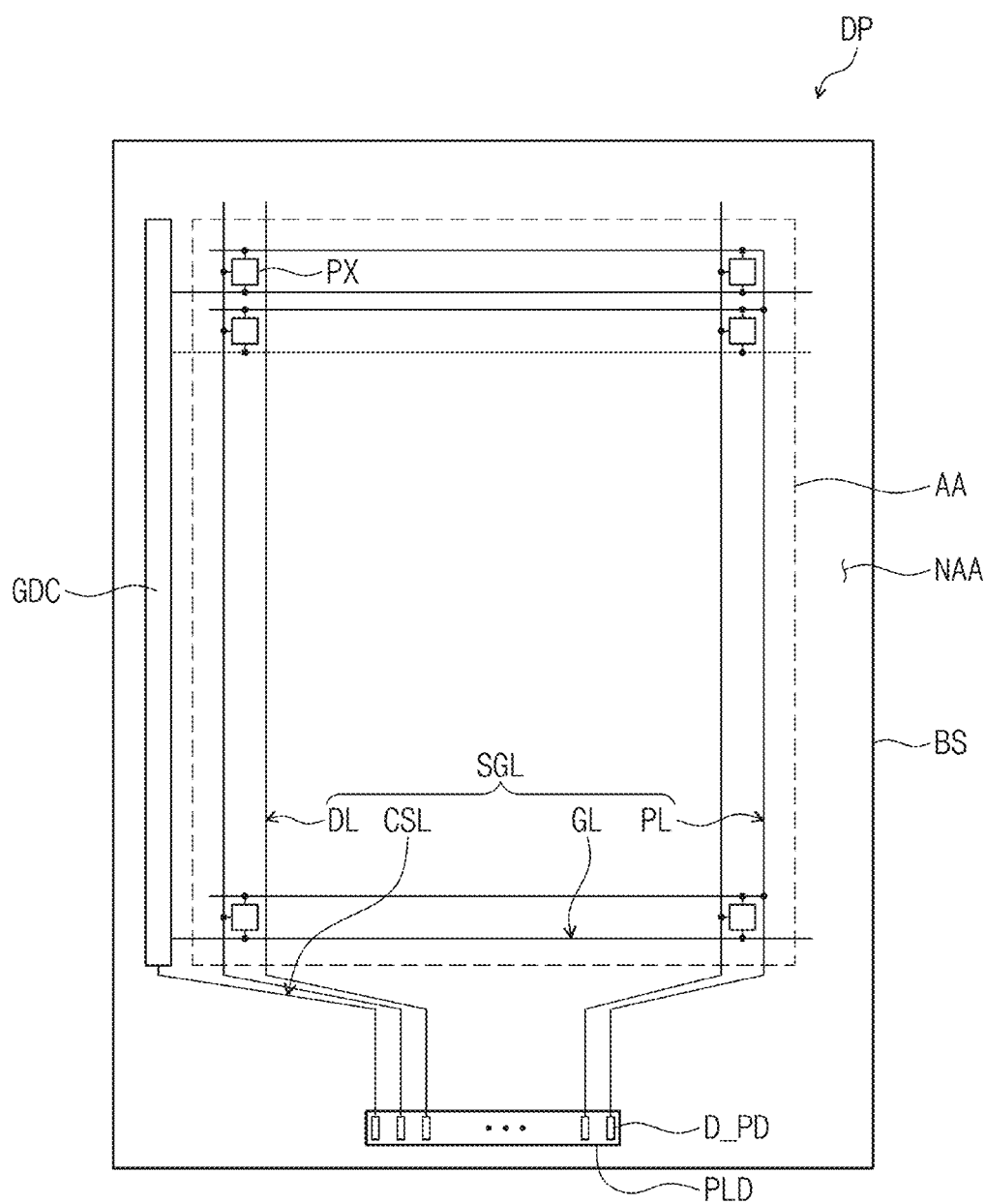
FIG. 2A is a plan view of an embodiment of a display panel of FIG. 1B.
Figure 2B:
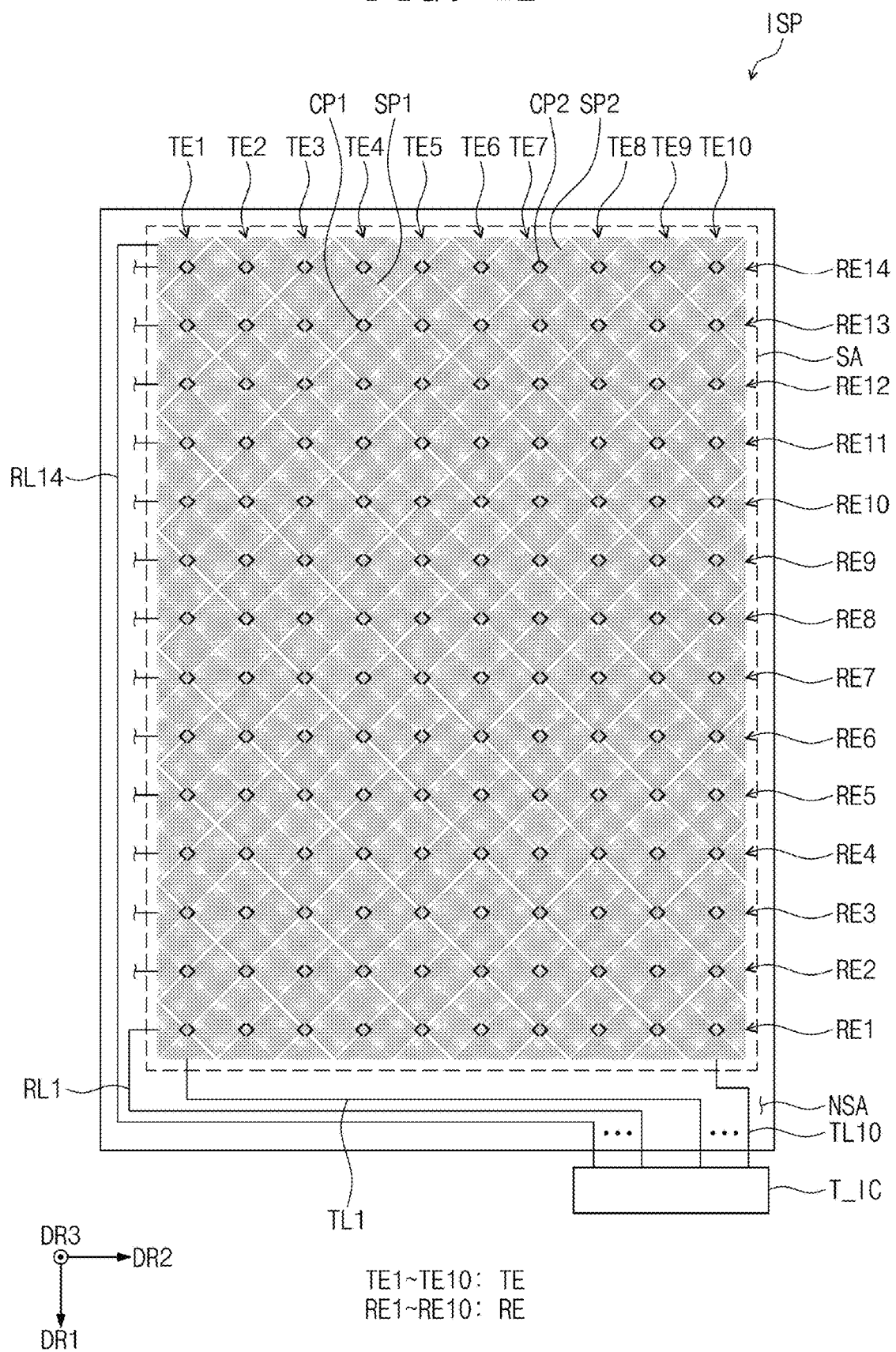
FIG. 2B is a plan view of an embodiment of an input sensor of FIG. 1B.
Figure 2C:
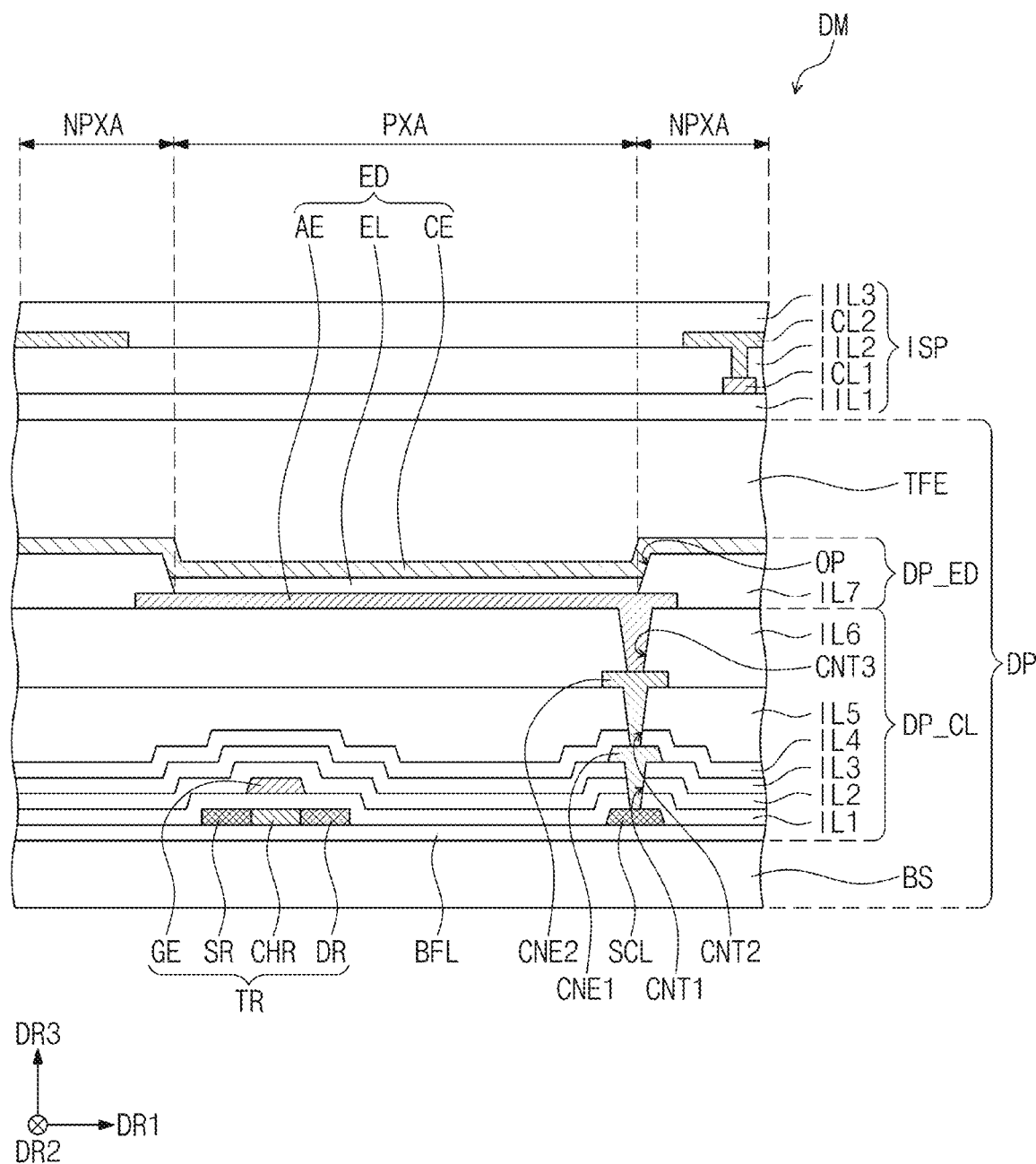
FIG. 2C is a cross-sectional view illustrating an embodiment of a display module of FIG. 1B.

FIG. 2A is a plan view showing the display panel DP according to an embodiment, FIG. 2B is a plan view showing the input sensor ISP according to an embodiment, and FIG. 2C is a cross-sectional view showing the display module DM according to an embodiment.

Referring to FIG. 2A, the display panel DP may include a driving circuit GDC, a plurality of signal lines SGL, and a plurality of pixels PX. The display panel DP may further include a pixel pad part PLD disposed in the peripheral area NAA. The pixel pad part PLD may include pixel pads D-PD each being connected to a corresponding signal line among the signal lines SGL.

The pixels PX may be arranged in the active area AA. Each of the pixels PX may include a light emitting element and a pixel driving circuit electrically connected to the light emitting element. The driving circuit GDC, the signal lines SGL, the pixel pad part PLD, and the pixel driving circuit may be included in a circuit layer DP_CL in FIG. 2C.

The driving circuit GDC may include a gate driving circuit. The gate driving circuit may generate a plurality of gate signals and may sequentially output the gate signals to a plurality of gate lines GL described later. The gate driving circuit may further output other control signals to the pixel driving circuit.

The signal lines SGL may include the gate lines GL, data lines DL, a power line PL, and a control signal line CSL. Each of the gate lines GL may be connected to a corresponding pixel among the pixels PX, and each of the data lines DL may be connected to a corresponding pixel among the pixels PX. The power line PL may be connected to the pixels PX. The control signal line CSL may provide control signals to the gate driving circuit. The signal lines SGL may overlap the active area AA and the peripheral area NAA.

The pixel PX may receive a gate signal from the gate line GL and a data signal from the data line DL. In addition, the pixel PX may receive a first source voltage from the power line PL. The light emitting element may include an organic light-emitting diode (i.e., an organic LED), a quantum dot, a quantum rod, a micro-LED, or a nano-LED.

The pixel pad part PLD may be connected to the flexible circuit film FCB, and the pixel pads D-PD may be disposed in the pixel pad part PLD. The pixel pads D-PD may be connected to corresponding pads of the flexible circuit film FCB. The pixel pads D-PD may be provided by exposing some of lines disposed in the circuit layer DP_CL without being covered by an insulating layer included in the circuit layer DP_CL. The pixel pads D-PD may be connected to corresponding pixels PX via the signal lines SGL. In addition, the driving circuit GDC may be connected to one pixel pad among the pixel pads D-PD.

Referring to FIG. 2B, the input sensor ISP may include a sensing area SA and a non-sensing area NSA. The sensing area SA may be activated in response to electrical signals. For example, the sensing area SA may be an area where the input is sensed or measured. The non-sensing area NSA may surround the sensing area SA. The sensing area SA may correspond to the active area AA of FIG. 2A, and the non-sensing area NSA may correspond to the peripheral area NAA of FIG. 2A.

The input sensor ISP may include a first electrode in the form of a transmission electrode part TE and a second electrode in the form of a reception electrode part RE. Alternatively, the input sensor ISP may include the first electrode in the form of the reception electrode part RE and the second electrode in the form of the transmission electrode part TE. The transmission electrode part TE and the reception electrode part RE may be disposed in the sensing area SA. The transmission electrode part TE may be electrically insulated from the reception electrode part RE in the sensing area SA while crossing the reception electrode part RE. The transmission electrode part TE may include n transmission electrodes (e.g., TE1 to TEn), and the reception electrode part RE may include m reception electrodes (e.g., RE1 to REn). In the descriptions, each of "n" and "m" is a natural number equal to or greater than 1. The "n" may be greater than the "m". However, embodiments are not limited thereto or thereby. For example, the "n" may be equal to or smaller than "m". As an example, in FIG. 2B, the transmission electrode part TE may include first to tenth transmission electrodes TE1 to TE10, and the reception electrode part RE may include first to fourteenth reception electrodes RE1 to RE14.

Each of the transmission electrodes TE1 to TE10 may extend in the first direction DR1 (e.g., in the column direction). The transmission electrodes TE1 to TE10 may be arranged in the second direction DR2 (e.g., in the row direction) to be spaced apart from each other. The transmission electrodes TE1 to TE10 may be electrically separated from each other. Each of the transmission electrodes TE1 to TE10 may include first sensing parts SP1 spaced apart from each other in the first direction DR1 and first connection parts CP1 electrically connecting the first sensing parts SP1. The first sensing parts SP1 and the first connection parts CP1 may be disposed on the different layers and may not be integrally formed with each other.

Each of the reception electrodes RE1 to RE14 may extend in the second direction DR2. The reception electrodes RE1 to RE14 may be arranged in the first direction DR1 to be spaced apart from each other. The reception electrodes RE1 to RE14 may be electrically separated from each other. The reception electrodes RE1 to RE14 may be disposed to cross the transmission electrodes TE1 to TE10 and may be electrically insulated from the transmission electrodes TE1 to TE10. Each of the reception electrodes RE1 to RE14 may include second sensing parts SP2 spaced apart from each other in the second direction DR2 and second connection parts CP2 electrically connecting the second sensing parts SP2. The second sensing parts SP2 may be integrally formed with the second connection parts CP2.

In FIG. 2C, the first sensing parts SP1 and the second sensing parts SP2 have a lozenge shape. However, embodiments are not limited thereto or thereby. For example, the first sensing parts SP1 and the second sensing parts SP2 may have different polygonal shapes from each other. Further, the first sensing parts SP1 and the second sensing parts SP2 may have various polygonal shapes.

Each of the transmission electrodes TE1 to TE10 and the reception electrodes RE1 to RE14 may have a mesh shape. As each of the transmission electrodes TE1 to TE10 and the reception electrodes RE1 to RE14 has the mesh shape, a parasitic capacitance between electrodes of the display panel DP (refer to FIG. 2A) and the transmission electrodes TE1 to TE10 and the reception electrodes RE1 to RE14 may be reduced.

The input sensor ISP may obtain the location information of the external input based on a variation of mutual capacitance between the transmission electrodes TE1 to TE10 and the reception electrodes RE1 to RE14. A mode in which the input sensor ISP is operated to obtain the location information of the external input may be defined as a first driving mode.

The input sensor ISP may further include a plurality of transmission lines TL1 to TL10 and a plurality of reception lines RL1 to RL14. The transmission lines TL1 to TL10 and the reception lines RL1 to RL14 may be disposed in the non-sensing area NSA. The transmission lines TL1 to TL10 may be electrically connected to one ends of the transmission electrodes TE1 to TE10, and the reception lines RL1 to RL14 may be electrically connected to one ends of the reception electrodes RE1 to RE14. However, embodiments are not limited thereto or thereby. As an example, the input sensor ISP may further include transmission lines electrically connected to the other ends of the transmission electrodes TE1 to TE10.

The input sensor ISP may be electrically connected to a sensor controller T_IC via the transmission lines TL1 to TL10 and the reception lines RL1 to RL14. The sensor controller T_IC may control a drive of the input sensor ISP. The sensor controller T_IC may be mounted on the main circuit board MCB in FIG. 1B in a chip form. The sensor controller T_IC may output transmission signals in the first driving mode, may apply the transmission signals to the transmission lines TL1 to TL10, and may receive a reception signal from the reception lines RL1 to RL14. In the first driving mode, the sensor controller T_IC may sequentially apply the transmission signals to the transmission lines TL1 to TL10, and the transmission electrodes TE1 to TE10 may sequentially receive the transmission signals. An electric potential of the reception electrodes RE1 to RE14 may be coupled or transferred to the transmission signals through the capacitance formed between the reception electrodes RE1 to RE14 and the transmission electrodes TE1 to TE10. The sensor controller T_IC may receive the coupled signal as the reception signal. When the touch event occurs by the user US (refer to FIG. 1A), the capacitance between the reception electrodes RE1 to RE14 and the transmission electrodes TE1 to TE10 is changed. As a result, the level of the reception signal generated when the touch event occurs is different from the level of the reception signal generated when the touch event does not occur. For example, a variation of the reception signal means a variation of the capacitance. Accordingly, the sensor controller T_IC may calculate the location information on a position at which the touch event by the user US, e.g., the external input TC (refer to FIG. 1A), occurs based on the variation of the capacitance between the reception electrodes RE1 to RE14 and the transmission electrodes TE1 to TE10.

Referring to FIG. 2C, the display module DM may include the display panel DP and the input sensor ISP disposed directly on the display panel DP. The display panel DP may include a base layer BS, the circuit layer DP_CL, a light emitting element layer DP_ED, and an encapsulation layer TFE.

The base layer BS may include a base surface (e.g., the upper surface) on which the circuit layer DP_CL is disposed. The base layer BS may be a glass substrate, a metal substrate, or a polymer substrate. However, embodiments are not limited thereto or thereby, and the base layer BS may be an inorganic layer, an organic layer, or a composite material layer.

The base layer BS may have a multi-layer structure. For instance, the base layer BS may have a three-layer structure with a synthetic resin layer, an adhesive layer, and a synthetic resin layer. The synthetic resin layer may include a polyimide-based resin. In addition, the synthetic resin layer may include at least one of an acrylic-based resin, a methacrylic-based resin, a polyisoprene-based resin, a vinyl-based resin, an epoxy-based resin, a urethane-based resin, a cellulose-based resin, a siloxane-based resin, a polyamide-based resin, and a perylene-based resin.

The circuit layer DP_CL may be disposed on the base layer BS. The circuit layer DP_CL may include an insulating layer, a semiconductor pattern, a conductive pattern, and a signal line. The insulating layer, a semiconductor layer, and a conductive layer may be formed on the base layer BS by a coating or depositing process. Then, the insulating layer, the semiconductor layer, and the conductive layer may be selectively patterned by several photolithography processes. The semiconductor pattern, the conductive pattern, and the signal line included in the circuit layer DP_CL may be formed.

At least one inorganic layer may be formed on an upper surface of the base layer BS. The inorganic layer may include at least one of aluminum oxide, titanium oxide, silicon oxide, silicon oxynitride, zirconium oxide, and hafnium oxide. The inorganic layer may be formed in multiple layers. The inorganic layers may form a barrier layer and/or a buffer layer. In an embodiment, the display layer DP may include a buffer layer BFL.

The buffer layer BFL may increase a coupling force between the base layer BS and the semiconductor pattern. The buffer layer BFL may include a silicon oxide layer and a silicon nitride layer, and the silicon oxide layer and the silicon nitride layer may be alternately stacked on each other.

The semiconductor pattern may be disposed on the buffer layer BFL. The semiconductor pattern may include polysilicon. However, embodiments are not limited thereto or thereby. The semiconductor pattern may include amorphous silicon or metal oxide.

FIG. 2C shows only a portion of the semiconductor pattern, and the semiconductor pattern may be further disposed in other areas. The semiconductor pattern may be arranged according to a specific order over the pixels. The semiconductor pattern may have different electrical properties according to whether or not it is doped or whether it is doped with an N-type dopant or a P-type dopant. The semiconductor pattern may include a doped region and a non-doped region. The doped region may be doped with the N-type dopant or the P-type dopant. A PMOS transistor may include a doped region doped with the P-type dopant, and an NMOS transistor may include a doped region doped with the N-type dopant.

The doped region may have a conductivity greater than that of the non-doped region and may substantially serve as an electrode or a signal line. The non-doped region may substantially correspond to a channel area of the transistor. In other words, a portion of the semiconductor pattern may be the channel area of the transistor, and other portions of the semiconductor pattern may be a source area or a drain area of the transistor.

Each of the pixels may include seven transistors, one capacitor, and the light emitting element. FIG. 2C shows one transistor TR and the light emitting element OLED included in the pixel.

A source area SR, a channel area CHR, and a drain area DR of the transistor TR may be formed from the semiconductor pattern. The source area SR and the drain area DR may extend in opposite directions to each other from the channel area CHR in a cross-sectional view. FIG. 2C shows a portion of the signal line SCL disposed on the same layer as the semiconductor pattern. For example, the signal line SCL may be electrically connected to the transistor TR, e.g., in a plane.

A first insulating layer IL1 may be disposed on the buffer layer BFL. The first insulating layer IL1 may commonly overlap the pixels and may cover the semiconductor pattern. The first insulating layer IL1 may be an inorganic layer and/or an organic layer and may have a single-layer or a multi-layer structure. The first insulating layer IL1 may include at least one of aluminum oxide, titanium oxide, silicon oxide, silicon oxynitride, zirconium oxide, and hafnium oxide. In an embodiment, the first insulating layer IL1 may have a single-layer structure with a silicon oxide layer. Not only the first insulating layer IL1, but also an insulating layer of the circuit layer DP_CL described later may be an inorganic layer and/or an organic layer and may have a single-layer or a multi-layer structure. The inorganic layer may include at least one of aluminum oxide, titanium oxide, silicon oxide, silicon oxynitride, zirconium oxide, and hafnium oxide. However, embodiments are not limited thereto.

A gate GE of the transistor TR may be disposed on the first insulating layer IL1. The gate GE may be a portion of a metal pattern. The gate GE may overlap the channel area CHR. The gate GE may be used as a mask in a doping process for the semiconductor pattern.

A second insulating layer IL2 may be disposed on the first insulating layer IL1 and may cover the gate GE. The second insulating layer IL2 may commonly overlap the pixels. The second insulating layer IL2 may be an inorganic layer and/or an organic layer and may have a single-layer or a multi-layer structure. In an embodiment, the second insulating layer IL2 may have a single-layer structure with a silicon oxide layer.

A third insulating layer IL3 may be disposed on the second insulating layer IL2. In an embodiment, the third insulating layer IL3 may have a single-layer structure with a silicon oxide layer.

A first connection electrode CNE1 may be disposed on the third insulating layer IL3. The first connection electrode CNE1 may be connected to the signal line SCL through a contact hole CNT1 passing through the first, second, and third insulating layers IL1, IL2, and IL3.

A fourth insulating layer IL4 may be disposed on the third insulating layer IL3. The fourth insulating layer IL4 may have a single-layer structure with a silicon oxide layer. A fifth insulating layer IL5 may be disposed on the fourth insulating layer IL4. The fifth insulating layer IL5 may be an organic layer.

A second connection electrode CNE2 may be disposed on the fifth insulating layer IL5. The second connection electrode CNE2 may be connected to the first connection electrode CNE1 through a contact hole CNT2 passing through the fourth insulating layer IL4 and the fifth insulating layer IL5.

A sixth insulating layer IL6 may be disposed on the fifth insulating layer IL5 and may cover the second connection electrode CNE2. The sixth insulating layer IL6 may be an organic layer. The light emitting element layer DP_ED may be disposed on the circuit layer DP_CL. The light emitting element layer DP_ED may include the light emitting element OLED. For example, the light emitting element OLED may include an organic LED, a quantum dot, a quantum rod, a micro-LED, or a nano-LED. The light emitting element OLED may include a first electrode AE, a light emitting layer EL, and a second electrode CE.

The first electrode AE may be disposed on the sixth insulating layer IL6. The first electrode AE may be connected to the second connection electrode CNE2 through a contact hole CNT3 passing through the sixth insulating layer IL6.

A pixel definition layer IL7 may be disposed on the sixth insulating layer IL6 and may cover a portion of the first electrode AE. An opening OP may be passing through the pixel definition layer IL7. At least a portion of the first electrode AE may be exposed through the opening OP of the pixel definition layer IL7. In an embodiment, a light emitting area PXA may be defined to correspond to the portion of the first electrode AE exposed through the opening OP. A non-light-emitting area NPXA may surround the light emitting area PXA.

The light emitting layer EL may be disposed on the first electrode AE. The light emitting layer EL may be disposed in the opening OP. For example, the light emitting layer EL may be formed in each of the pixels after being divided into plural portions. When the light emitting layer EL is formed in each of the pixels after being divided into plural portions, each of the light emitting layers EL may emit a light having at least one of blue, red, and green colors. However, embodiments are not limited thereto or thereby. The light emitting layer EL may be connected to the pixels and may be commonly provided. In this case, the light emitting layer EL may emit a blue light or a white light.

The second electrode CE may be disposed on the light emitting layer EL. The second electrode CE may have an integral shape and may be commonly disposed over the pixels. A common voltage may be applied to the second electrode CE, and the second electrode CE may be referred to as a common electrode.

For example, a hole control layer may be disposed between the first electrode AE and the light emitting layer EL. The hole control layer may be commonly disposed in the light emitting area PXA and the non-light-emitting area NPXA. The hole control layer may include a hole transport layer and may further include a hole injection layer. An electron control layer may be disposed between the light emitting layer EL and the second electrode CE. The electron control layer may include an electron transport layer and may further include an electron injection layer. The hole control layer and the electron control layer may be commonly formed in the plural pixels by using an open mask. An encapsulation layer TFE may be disposed on the light emitting element layer DP_ED. The encapsulation layer TFE may include an inorganic layer, an organic layer, and an inorganic layer, which are sequentially stacked. However, embodiments are not limited thereto or thereby.

The inorganic layers may protect the light emitting element layer DP_ED from moisture and oxygen, and the organic layer may protect the light emitting element layer DP_ED from foreign substances such as dust particles. The inorganic layers may include a silicon nitride layer, a silicon oxynitride layer, a silicon oxide layer, a titanium oxide layer, or an aluminum oxide layer. The organic layer may include an acrylic-based organic layer. However, embodiments are not limited thereto or thereby.

The input sensor ISP may be formed on the display panel DP by successive processes. The input sensor ISP may include a base insulating layer IIL1, a first conductive layer ICL1, and a sensing insulating layer IIL2, a second conductive layer ICL2, and a cover insulating layer IIL3.

The base insulating layer IIL1 may be an inorganic layer including one of silicon nitride, silicon oxynitride, and silicon oxide. As another way, the base insulating layer IIL1 may include an organic layer including an epoxy-based resin, an acrylic-based resin, or an imide-based resin. The base insulating layer IIL1 may have a single-layer structure or a multi-layer structure with layers stacked in the third direction DR3.

The first conductive layer ICL1 may be disposed on the base insulating layer IIL1. As an example, the first conductive layer ICL1 may include the first connection parts CP1. The first conductive layer ICL1 may be covered by the sensing insulating layer IIL2. The second conductive layer ICL2 may be disposed on the sensing insulating layer IIL2. The second conductive layer ICL2 may include the first and second sensing parts SP1 and SP2 and the second connection parts CP2. FIG. 2C shows a structure in which the first and second sensing parts SP1 and SP2 are included in the second conductive layer ICL2 disposed above the first io conductive layer ICL1 to improve a sensitivity. However, embodiments are not limited thereto or thereby. For example, the first and second sensing parts SP1 and SP2 may be included in the first conductive layer ICL1.

Each of the first conductive layer ICL1 and the second conductive layer ICL1 may have a single-layer structure or a multi-layer structure with layers stacked in the third is direction DR3. The conductive layer having the single-layer structure may include a metal layer or a transparent conductive layer. The metal layer may include molybdenum, silver, titanium, copper, aluminum, or alloys thereof. The transparent conductive layer may include a transparent conductive oxide, such as indium tin oxide (ITO), indium zinc oxide (IZO), zinc oxide (ZnO), indium zinc tin oxide (ITZO), or the like. In addition, the transparent conductive layer may include a conductive polymer such as PEDOT, a metal nanowire, a graphene, or the like.

The conductive layer having the multi-layer structure may include metal layers. As an example, the metal layers may have a three-layer structure of titanium/aluminum/titanium. The conductive layer having the multi-layer structure may include at least one metal layer and at least one transparent conductive layer.

At least one of the sensing insulating layer IIL2 and the cover insulating layer IIL3 may include an inorganic layer. The inorganic layer may include at least one of aluminum oxide, titanium oxide, silicon oxide, silicon oxynitride, zirconium oxide, and hafnium oxide.

At least one of the sensing insulating layer IIL2 and the cover insulating layer IIL3 may include an organic layer. The organic layer may include at least one of an acrylic-based resin, a methacrylic-based resin, a polyisoprene-based resin, a vinyl-based resin, an epoxy-based resin, a urethane-based resin, a cellulose-based resin, a siloxane-based resin, a polyimide-based resin, a polyamide-based resin, and a perylene-based resin.

Figure 3:
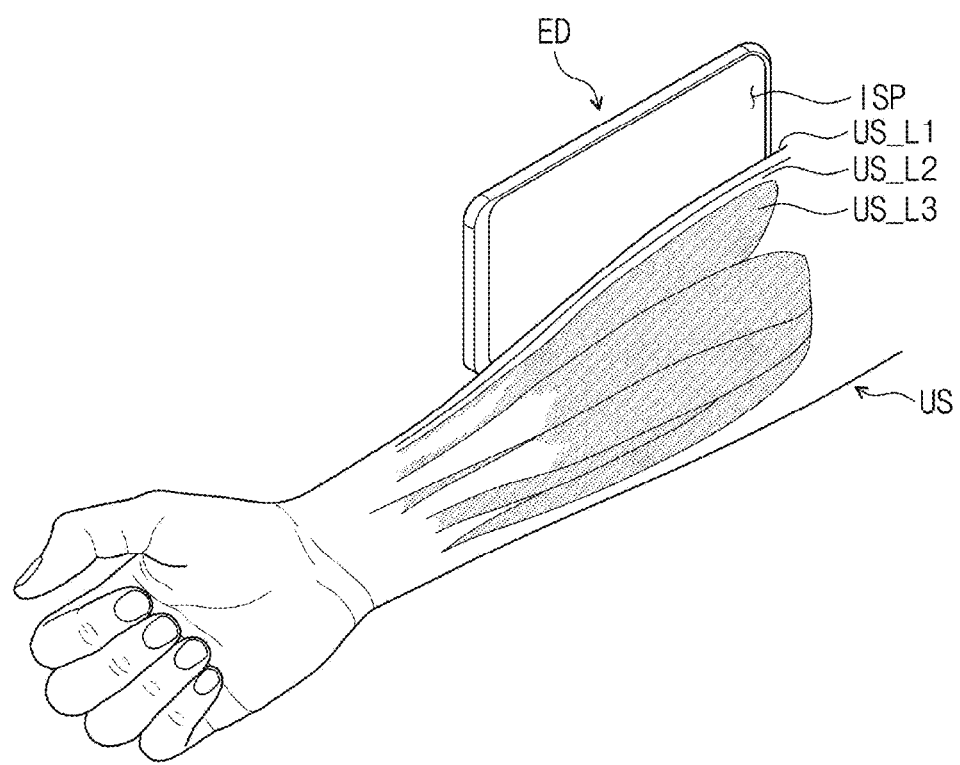
FIG. 3 is a view illustrating a state in which a body composition of a user is measured using the electronic device of FIG. 1A according to an embodiment.
Figure 4A:
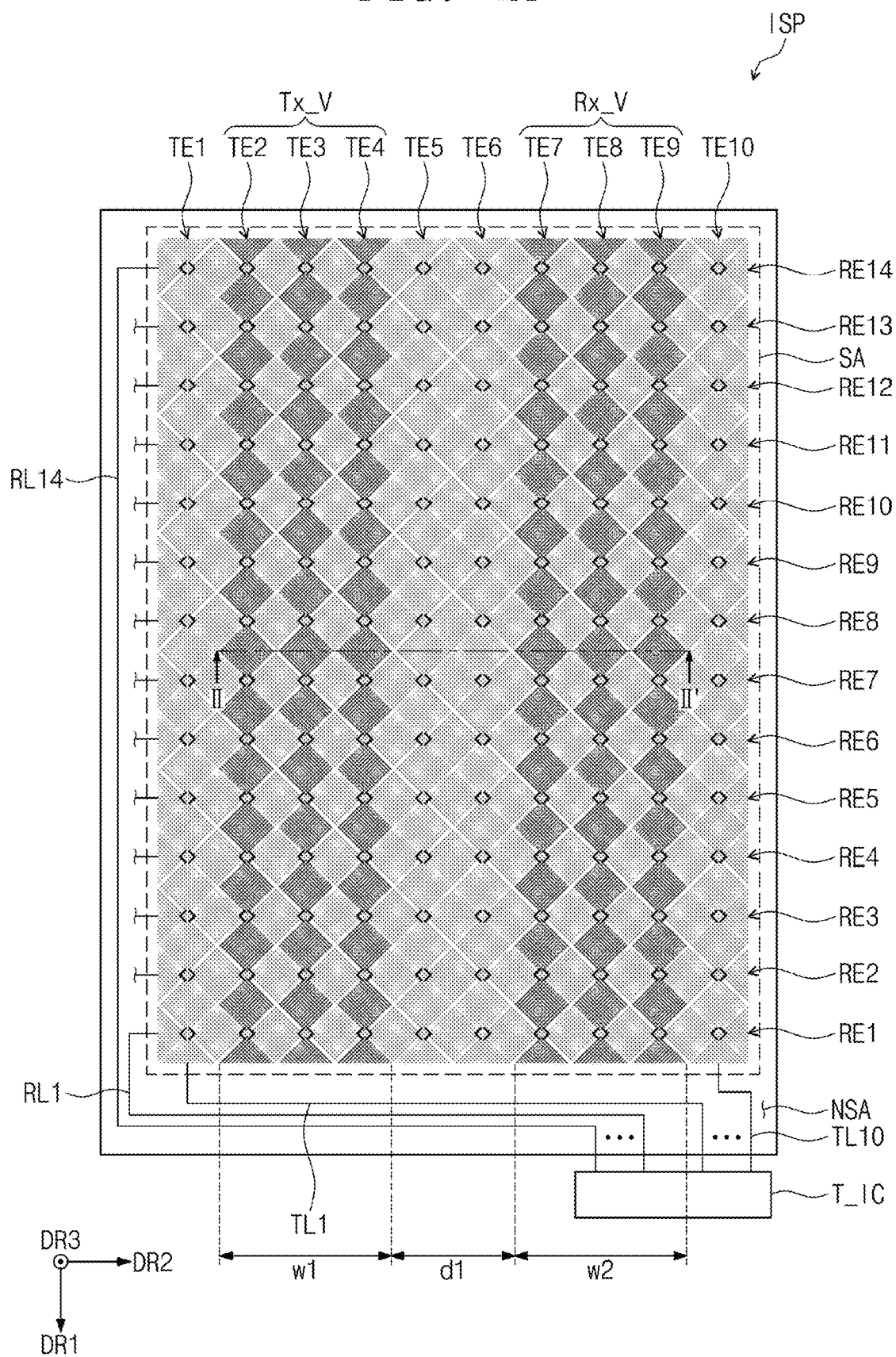
FIG. 4A is a plan view of the input sensor of FIG. 1B illustrating an operation thereof in a second driving mode according to an embodiment.
Figure 4B:
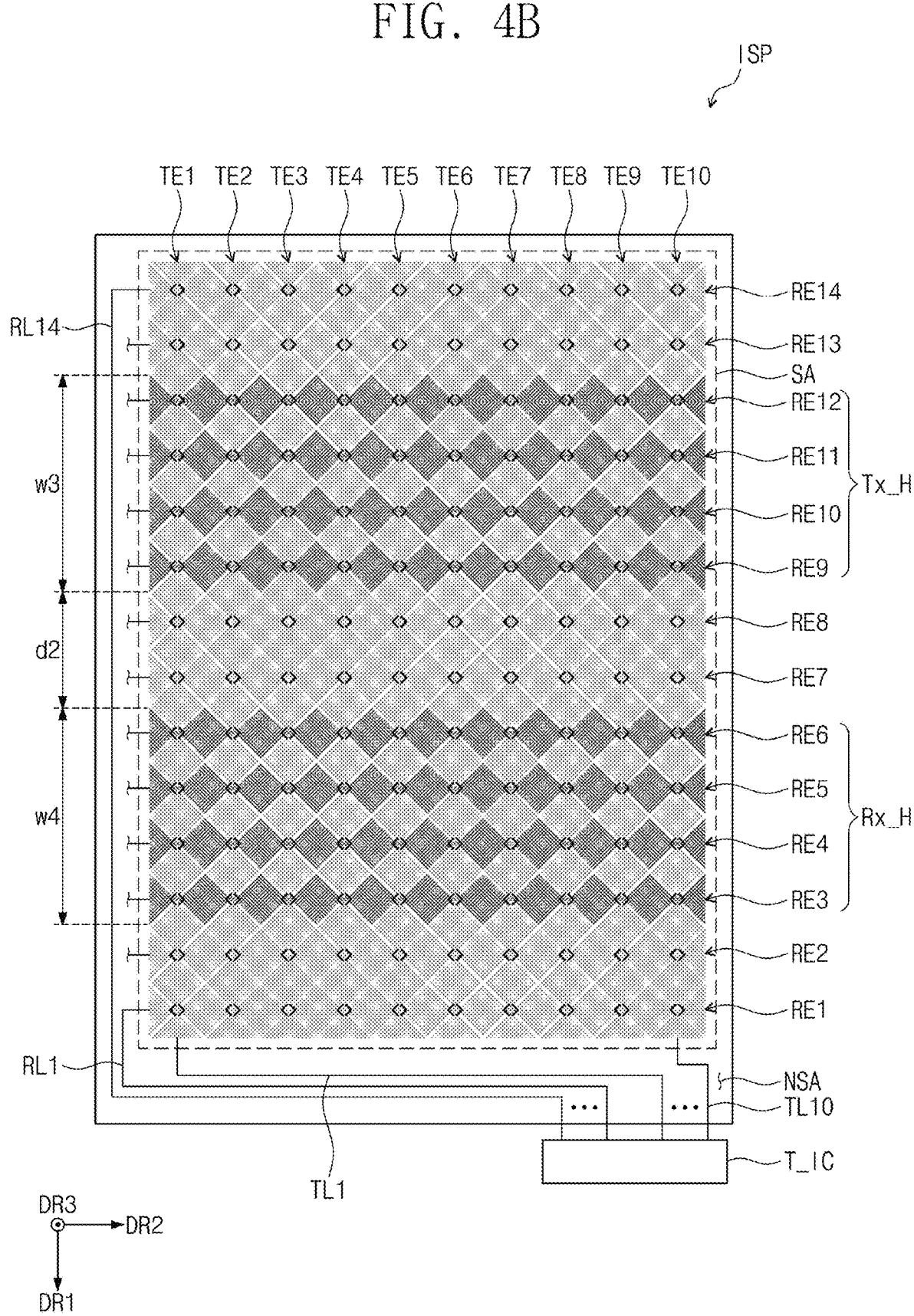
FIG. 4B is a plan view of the input sensor of FIG. 1B illustrating an operation thereof in a second driving mode according to an embodiment.
Figure 5:
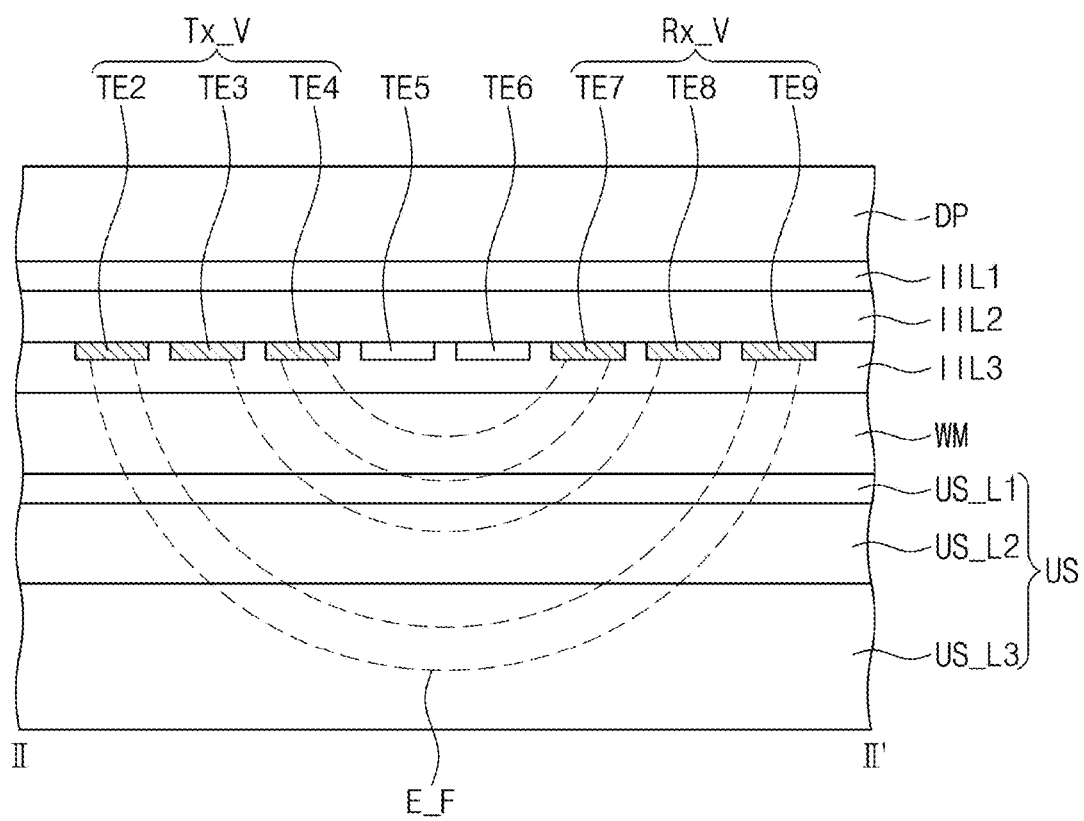
FIG. 5 is a cross-sectional view of the input sensor of FIG. 1B illustrating an operational principle thereof in a second driving mode according to an embodiment.

FIG. 3 is a view showing a state in which a body composition of the user US is measured using the electronic device ED according to an embodiment. FIGS. 4A and 4B are plan views showing the input sensor ISP operated in a second driving mode. FIG. 5 is a view showing an operational principle of the input sensor operated in the second driving mode according to an embodiment.

Referring to FIG. 3, the electronic device ED may have a function that analyzes the body composition of the user US. The electronic device ED may obtain information on the body composition of the user US by using the input sensor ISP. A mode in which the input sensor ISP is operated to obtain the information on the body composition of the user US may be referred to as the second driving mode. As an example, the body composition may include a muscle mass, a body fat mass, a moisture level, or the like.

When the input sensor ISP is operated in the second driving mode, the body composition of the user US may be measured using some of the transmission electrodes TE1 to TE10 or some of the reception electrodes RE1 to RE14. Hereinafter, electrodes used in the second driving mode may be defined as a transmission sensing electrode and a reception sensing electrode. In particular, as shown in FIG. 4A, a case where some of the transmission electrodes TE1 to TE10 are used as a transmission sensing electrode Tx_V and a reception sensing electrode Rx_V is referred to as a vertical measuring mode, and as shown in FIG.4B, a case where some of the reception electrodes RE1 to RE14 are used as a transmission sensing electrode Tx_H and a reception sensing electrode Rx_H is referred to as a horizontal measuring mode. For example, in the vertical measuring mode, the input sensor ISP may operate by using mutual capacitance between at least two groups among the reception electrodes RE1 to RE14, which are substantially parallel to each other, and do not intersect each other in a plan view. For example, in the horizontal measuring mode, the input sensor ISP may operate by using mutual capacitance between at least two groups among the transmission electrodes TE1 to TE10, which are substantially parallel to each other, and do not intersect each other in a plan view.

Referring to FIGS. 4A and 5, in the vertical measuring mode, the input sensor ISP may obtain the information on the body composition of the user US based on a variation of mutual capacitance between the transmission sensing electrode Tx_V and the reception sensing electrode Rx_V.

The transmission sensing electrode Tx_V may include a first group among the transmission electrodes TE1 to TE10, and the reception sensing electrode Rx_V may include a second group among the transmission electrodes TE1 to TE10. The transmission sensing electrode Tx_V may include k transmission electrodes, and the reception sensing electrode Rx_V may include j transmission electrodes. In the descriptions, each of "k" and "j" may be a natural number greater than 1 and smaller than n/2, and the "k" and the "j" may be the same as each other or may be different from each other. In an embodiment shown in FIG. 4A, each of the "k" and the "j" is 3. However, embodiments are not limited thereto or thereby.

When the input sensor ISP is operated in the second driving mode, an electric field E_F may be formed between the transmission sensing electrode Tx_V and the reception sensing electrode Rx_V. An intensity of the electric field E_F and a depth of penetration of the electric field E_F may be determined by a width w1 of the transmission sensing electrode Tx_V, a width w2 of the reception sensing electrode Rx_V, and a distance d1 between the transmission sensing electrode Tx_V and the reception sensing electrode Rx_V. As the width w1 of the transmission sensing electrode Tx_V, the width w2 of the reception sensing electrode Rx_V, and the distance d1 between the transmission sensing electrode Tx_V and the reception sensing electrode Rx_V decrease, the intensity of the electric field E_F may increase. However, the depth of penetration of the electric field E_F may increase as the distance d1 between the transmission sensing electrode Tx_V and the reception sensing electrode Rx_V increases. When the depth of penetration of the electric field E_F decreases, it is difficult to measure the body composition located deep within the body of the user US, for example, the muscle mass. In other words, the intensity of the electric field E_F and the depth of penetration of the electric field E_F may have a trade-off relationship. Accordingly, the width w1 of the transmission sensing electrode Tx_V, the width w2 of the reception sensing electrode Rx_V, and the distance d1 between the transmission sensing electrode Tx_V and the reception sensing electrode Rx_V may be determined by taking into account the intensity and the depth of penetration of the electric field E_F.

In an embodiment, the width w1 of the transmission sensing electrode Tx_V may be determined by the number of the transmission electrodes included in the transmission sensing electrode Tx_V, and the width w2 of the reception sensing electrode Rx_V may be determined by the number of the transmission electrodes included in the reception sensing electrode Rx_V. In FIGS. 4A and 5, the transmission sensing electrode Tx_V may include second, third, and fourth transmission electrodes TE2, TE3, and TE4, and the reception sensing electrode Rx_V may include seventh, eighth, and ninth transmission electrodes TE7, TE8, and TE9. The transmission sensing electrode Tx_V may be spaced apart from the reception sensing electrode Rx_V in the second direction DR2 by the distance d1.

For the convenience of explanation, FIG. 5 shows a structure in which each of the second, third, and fourth transmission electrodes TE2, TE3, and TE4 has an integral pattern structure (e.g., a solid pattern structure). However, the structure of each of the second, third, and fourth transmission electrodes TE2, TE3, and TE4 should not be limited thereto or thereby. For example, each of the second, third, and fourth transmission electrodes TE2, TE3, and TE4 may have a structure patterned to have a mesh pattern. Similarly, in FIG. 5, each of the seventh, eighth, and ninth transmission electrodes TE7, TE8, and TE9 has an integral pattern structure (e.g., a solid pattern structure), however, each of the seventh, eighth, and ninth transmission electrodes TE7, TE8, and TE9 may have a structure patterned to have a mesh pattern.

In the vertical measuring mode, transmission electrodes TE1, TES, TE6, and TE10 that are not used as the transmission sensing electrode Tx_V and the reception sensing electrode Rx_V are referred to as a peripheral transmission electrode.

In the second driving mode, the sensor controller T_IC may transmit a transmission sensing signal to the transmission sensing electrode Tx_V and may receive a reception sensing signal from the reception sensing electrode Rx_V. For example, the sensor controller T_IC may control the input sensor ISP to operate in the second driving mode.

When the electronic device ED is in contact with the body of the user US while the input sensor ISP is operated in the second driving mode, a capacitance between the transmission sensing electrode Tx_V and the reception sensing electrode Rx_V may vary according to the body composition of the user US. For example, in the human body, each of a skin layer US_L1, a subcutaneous fat layer US_L2, and a muscle layer US_L3 has different dielectric constants from each other. The dielectric constant of the muscle layer US_L3 may be smaller than the dielectric constant of the subcutaneous fat layer US_L2. Accordingly, as the subcutaneous fat layer US_L2 increases in thickness, the capacitance between the transmission sensing electrode Tx_V and the reception sensing electrode Rx_V may increase. As the io subcutaneous fat layer US_L2 decreases in thickness and the muscle layer US_L3 increases in thickness, the capacitance between the transmission sensing electrode Tx_V and the reception sensing electrode Rx_V may decrease. As described above, the sensor controller T_IC may measure the body composition of the user US based on the capacitance measured by the input sensor ISP operated in the second driving mode.

Referring to FIG. 4B, in the horizontal measuring mode, the input sensor ISP may obtain the information on the body composition of the user US based on the variation of the mutual capacitance between the transmission sensing electrode Tx_H and the reception sensing electrode Rx_H.

The transmission sensing electrode Tx_H may include a first group among the reception electrodes RE1 to RE14, and the reception sensing electrode Rx_H may include a second group among the reception electrodes RE1 to RE14. The transmission sensing electrode Tx_H may include p reception electrodes, and the reception sensing electrode Rx_H may include q reception electrodes. In an embodiment, each of "p" and "q" may be a natural number greater than 1 and smaller than m/2, and the "p" and the "q" may be the same as each other or may be different from each other. In an embodiment shown in FIG. 4B, each of the "p" and the "q" is 4, however, embodiments are not limited thereto or thereby.

When the input sensor ISP is operated in the second driving mode, the electric field E_F (refer to FIG. 5) may be formed between the transmission sensing electrode Tx_H and the reception sensing electrode Rx_H. The intensity and the depth of penetration of the electric field E_F may be determined by a width w3 of the transmission sensing electrode Tx_H, a width w4 of the reception sensing electrode Rx H, and a distance d2 between the transmission sensing electrode Tx_H and the reception sensing electrode Rx_H. In an embodiment, the width w3 of the transmission sensing electrode Tx_H may be determined by the number of the reception electrodes included in the transmission sensing electrode Tx_H, and the width w4 of the reception sensing electrode Rx_H may be determined by the number of the reception electrodes included in the reception sensing electrode Rx_H. In FIG. 4B, the transmission sensing electrode Tx_H may include ninth, tenth, eleventh, and twelfth reception electrodes RE9, RE10, RE11, and RE12, and the reception sensing electrode Rx_H may include third, fourth, fifth, and sixth reception electrodes RE3, RE4, RE5, and RE6. The transmission sensing electrode Tx_H may be spaced apart from the reception sensing electrode Rx_H in the first direction DR1 by the distance d2.

In the horizontal measuring mode, reception electrodes RE1, RE2, RE7, RE8, RE13, and RE14 that are not used as the transmission sensing electrode Tx_H and the reception sensing electrode Rx_H are referred to as a peripheral reception electrode.

When the electronic device ED is in contact with the body of the user US while the input sensor ISP is operated in the second driving mode, the capacitance between the transmission sensing electrode Tx_H and the reception sensing electrode Rx_H may vary according to the body composition of the user US. For example, the sensor controller T_IC may measure the body composition of the user US based on the capacitance measured by the input sensor ISP operated in the second driving mode.

Figure 6A:
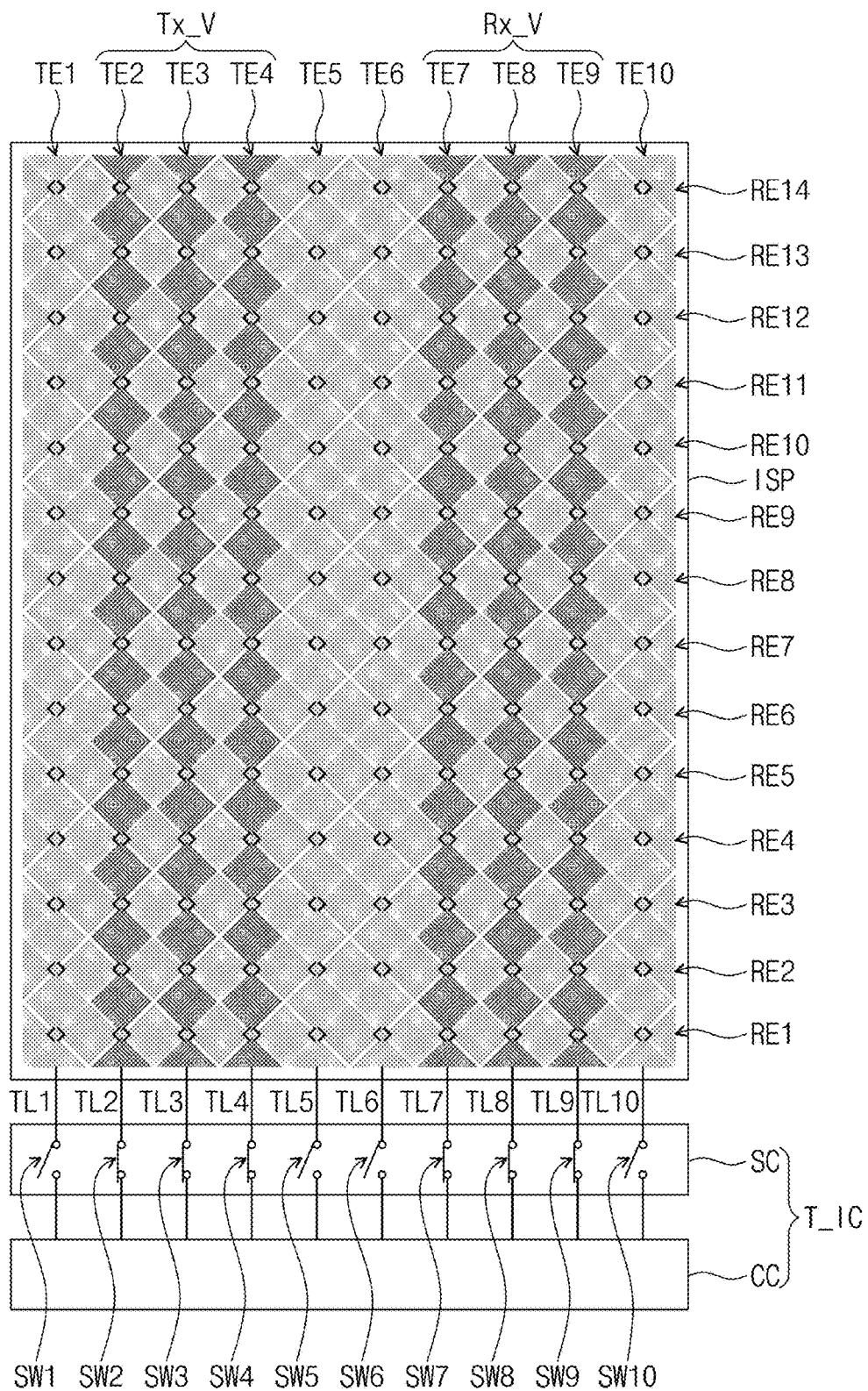
FIG. 6A is a view of the input sensor of FIG. 1B illustrating an operation of a sensor controller in a second driving mode according to an embodiment.
Figure 6B:
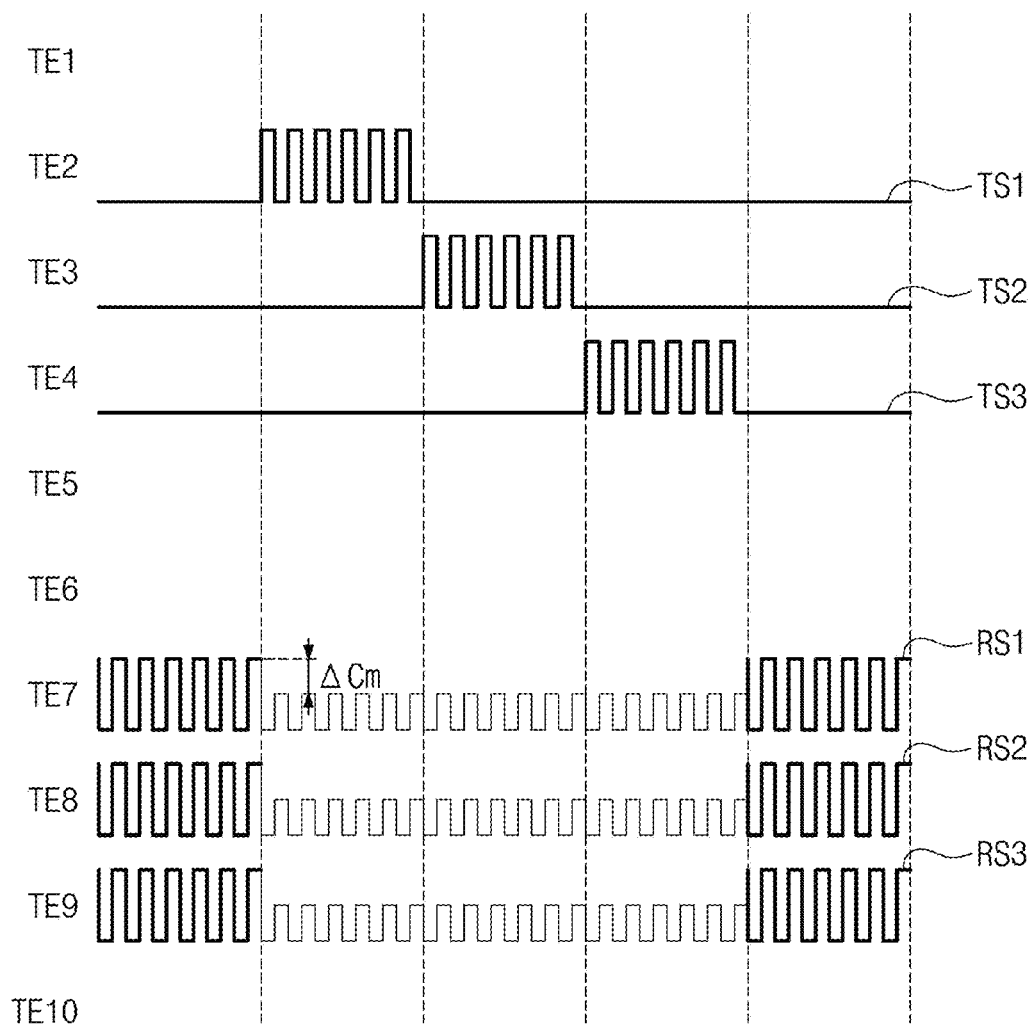
FIGS. 6B and 6C are waveform diagrams illustrating waveforms of a transmission sensing signal applied to the input sensor shown in FIG. 6A and a reception sensing signal output from the input sensor shown in FIG. 6A according to an embodiment.
Figure 6C:
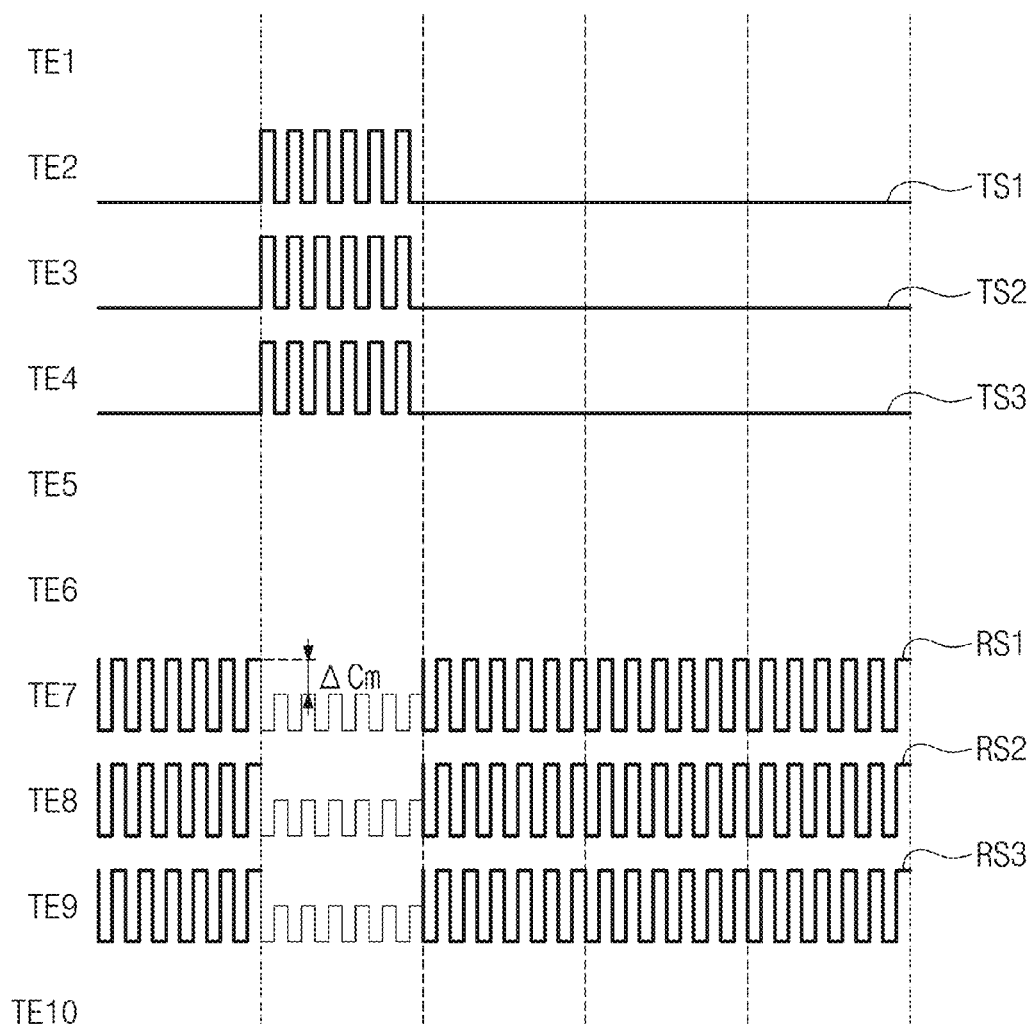

FIG. 6A is a view showing an operation of the sensor controller T IC in the second driving mode according to an embodiment. FIGS. 6B and 6C are waveform diagrams showing waveforms of the transmission sensing signal applied to the input sensor shown in FIG. 6A and the reception sensing signal output from the input sensor shown in FIG. 6A.

Referring to FIG. 6A, the sensor controller T_IC may include a switching circuit io SC and a control circuit CC. The switching circuit SC may include a plurality of switching devices SW1 to SW10 respectively connected to the transmission lines TL1 to TL10. In the first driving mode, all the switching devices SW1 to SW10 may be in a turned-on state, and in the second driving mode, only some of the switching devices SW1 to SW10 may be in the turned-on state. As an example, in the second driving mode, the second, third, fourth, seventh, eighth, and ninth switching devices SW2, SW3, SW4, SW7, SW8, and SW9 among the switching devices SW1 to SW10 may be turned on, and the first, fifth, sixth, and tenth switching devices SW1, SW5, SW6, and SW10 among the switching devices SW1 to SW10 may be turned off.

The control circuit CC may control a drive of the switching circuit SC according to the first and second driving modes. In the second driving mode, the sensor controller T_IC may apply the transmission sensing signal to the transmission sensing electrode Tx_V via the turned-on second, third, and fourth switching devices SW2, SW3, and SW4. In addition, in the second driving mode, the sensor controller T_IC may receive the reception sensing signal from the reception sensing electrode Rx_V via the turned-on seventh, eighth, and ninth switching devices SW7, SW8, and SW9.

Referring to FIG. 6B, the transmission sensing signal may include first, second, and third transmission sensing signals TS1, TS2, and TS3. The first transmission sensing signal TS1 may be applied to the second transmission electrode TE2 via a second transmission line TL2, and the second transmission sensing signal TS2 may be applied to the third transmission electrode TE3 via a third transmission line TL3. The third transmission sensing signal TS3 may be applied to the fourth transmission electrode TE4 via a fourth transmission line TL4. The first, second, and third transmission sensing signals TS1, TS2, and TS3 may be sequentially applied to the second, third, and fourth transmission lines TL2, TL3, and TL4.

The reception sensing signal may include first, second, and third reception sensing signals RS1, RS2, and RS3. The first, second, and third reception sensing signals RS1, RS2, and RS3 may be signals respectively output from the seventh, eighth, and ninth transmission electrodes TE7, TE8, and TE9. The first reception sensing signal RS1 may be applied to the sensor controller T_IC via a seventh transmission line TL7, and the second is reception sensing signal RS2 may be applied to the sensor controller T_IC via an eighth transmission line TL8. The third reception sensing signal RS3 may be applied to the sensor controller T_IC via a ninth transmission line TL9. The sensor controller T_IC may sequentially receive the first, second, and third reception sensing signals RS1, RS2, and RS3. Alternatively, the sensor controller T_IC may substantially simultaneously receive the first, second, and third reception sensing signals RS1, RS2, and RS3.

The peripheral transmission electrodes TE1, TE5, TE6, and TE10 may be in a floating state by the turned-off switching devices SW1, SW5, SW6, and SW10.

According to FIG. 6C, the first, second, and third transmission sensing signals TS1, TS2, and TS3 may be substantially simultaneously applied to the first, second, and third transmission lines TL1, TL2, and TL3, respectively. In addition, the sensor controller T_IC may substantially simultaneously receive the first, second, and third reception sensing signals RS1, RS2, and RS3.

As shown in FIGS. 6B and 6C, the capacitance according to the body composition of the user US may be reflected or applied to each of the first, second, and third reception sensing signals RS1, RS2, and RS3. The body composition of the user US may be measured based on the variation ACm obtained by comparing the capacitance measured through the first, second, and third reception sensing signals RS1, RS2, and RS3 with a predetermined reference capacitance.

FIGS. 6A, 6B, and 6C shows the sensor controller T_IC operated in the vertical measuring mode, however, the sensor controller T_IC may be operated similarly in the horizontal measuring mode.

Figure 7A:
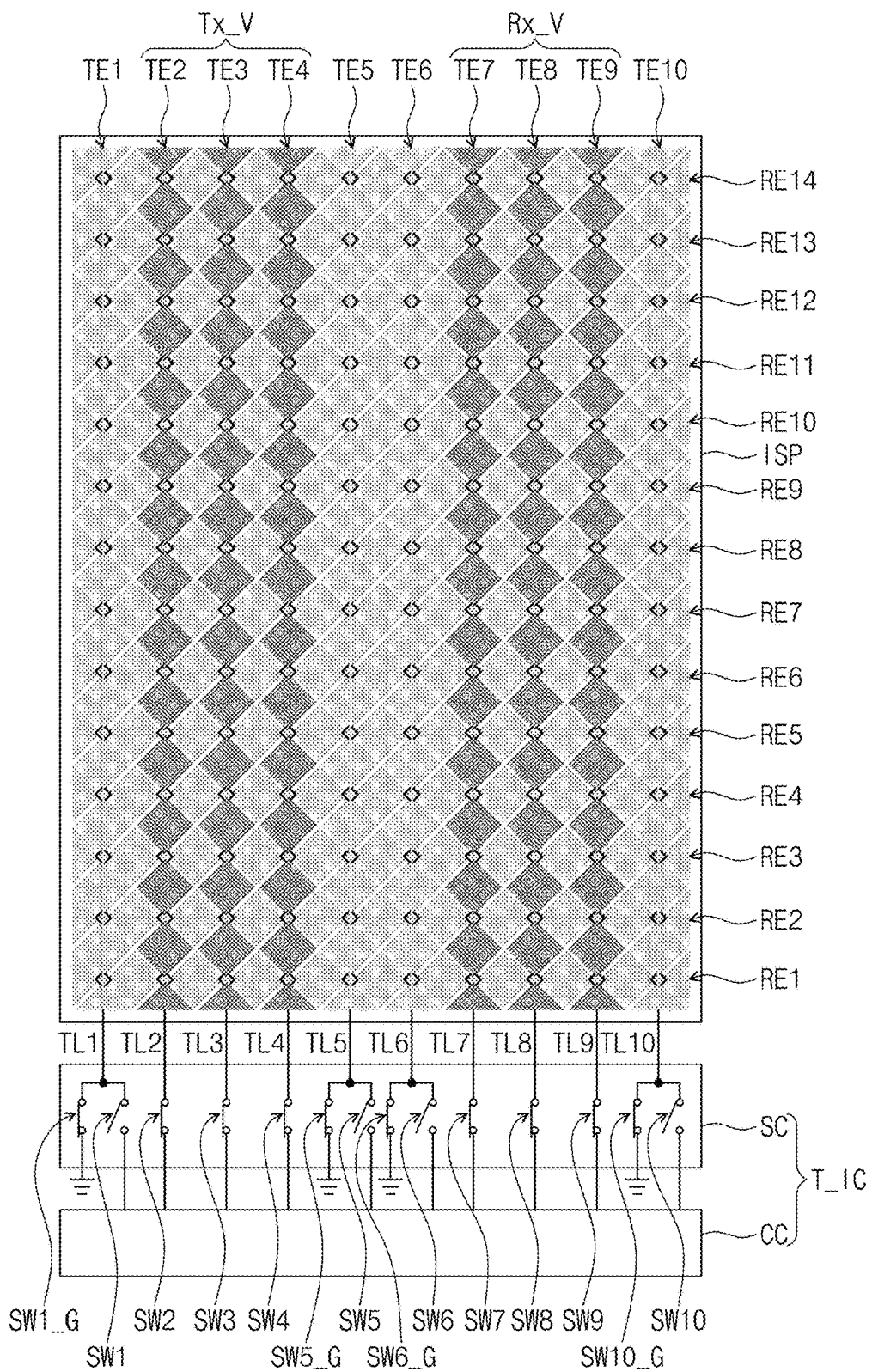
FIG. 7A is a view illustrating an operation of a sensor controller in a second driving mode according to an embodiment.
Figure 7B:
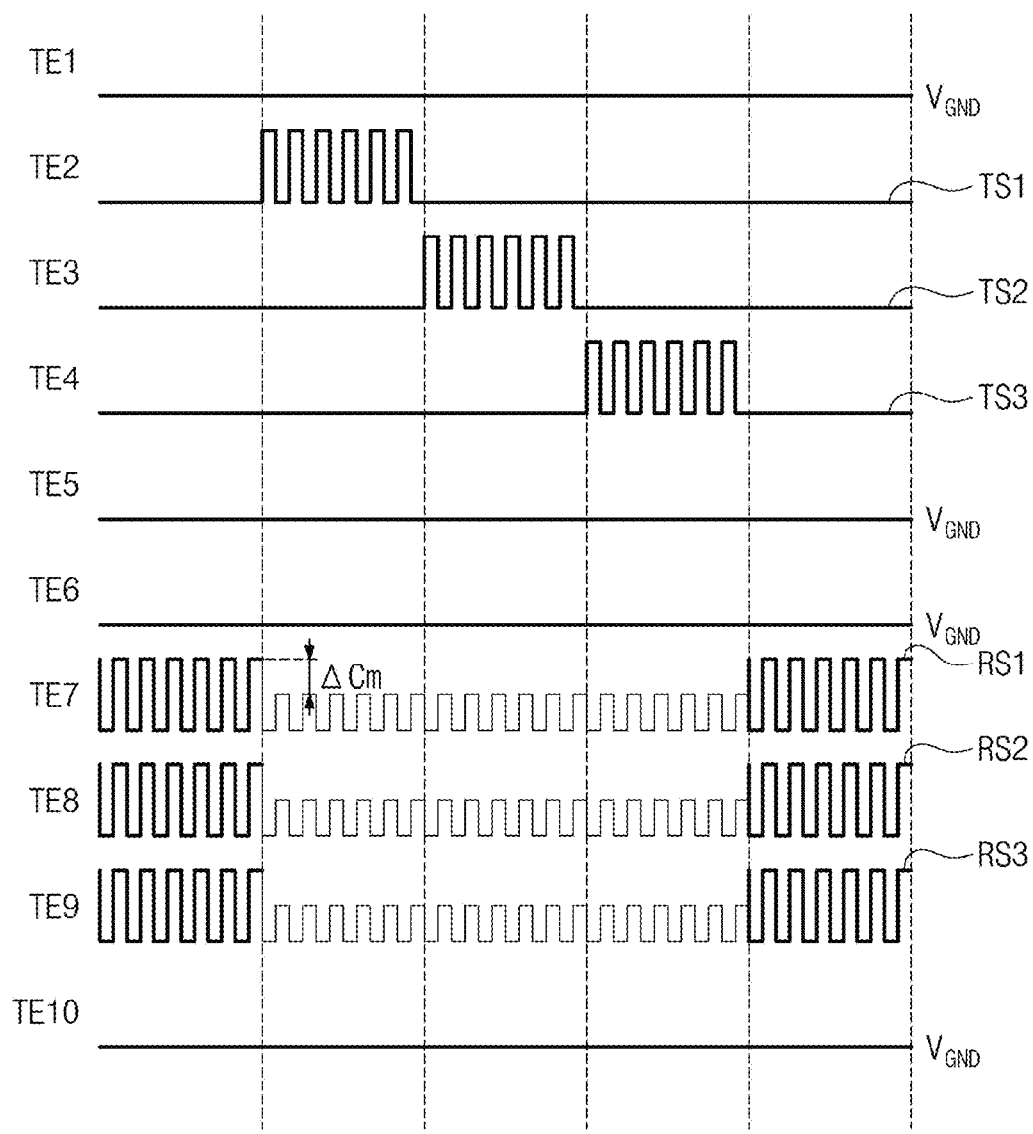
FIG. 7B is a waveform diagram illustrating waveforms of a transmission sensing signal applied to an input sensor shown in FIG. 7A and a reception sensing signal output from the input sensor shown in FIG. 7A according to an embodiment.

FIG. 7A is a view showing an operation of a sensor controller T_IC in a second driving mode according to an embodiment, and FIG. 7B is a waveform diagram showing waveforms of a transmission sensing signal applied to the input sensor T_IC shown in FIG. 7A and a reception sensing signal output from the input sensor T_IC shown in FIG. 7A.

Referring to FIG. 7A, the sensor controller T_IC may include a switching circuit SC and a control circuit CC. The switching circuit SC may include a plurality of switching devices SW1 to SW10 respectively connected to transmission lines TL1 to TL10. The switching circuit SC may further include ground switching devices SW1_G, SW5_G, SW6_G, and SW10_G. The ground switching devices SW1_G, SW5_G, SW6_G, and SW10_G may be electrically connected to peripheral transmission lines TL1, TL5, TL6, and TL10 connected to peripheral transmission electrodes TE1, TE5, TE6, and TE10.

In the first driving mode, all the switching devices SW1 to SW10 may be in a turned-on state, and the ground switching devices SW1_G, SW5_G, SW6_G, and SW10_G may be in a turned-off state. In the second driving mode, only some of the switching devices SW1 to SW10 may be in the turned-on state. As an example, in the second driving mode, second, third, fourth, seventh, eighth, and ninth switching devices SW2, SW3, SW4, SW7, SW8, and SW9 among the switching devices SW1 to SW10 may be turned on, and first, fifth, sixth, and tenth switching devices SW1, SW5, SW6, and SW10 among the switching devices SW1 to SW10 may be turned off. In the second driving mode, the ground switching devices SW1_G, SW5_G, SW6_G, and SW10 _G may be in the turned-on state.

The control circuit CC may control a drive of the switching circuit SC according to the first and second driving modes. In the second driving mode, the sensor controller T_IC may apply a transmission sensing signal to a transmission sensing electrode Tx_V via the turned-on second, third, and fourth switching devices SW2, SW3, and SW4. In addition, in the second driving mode, the sensor controller T_IC may receive a reception sensing signal from a reception sensing electrode Rx_V via the turned-on seventh, eighth, and ninth switching devices SW7, SW8, SW9.

According to FIG. 7B, a ground voltage $V_{GND}$ may be applied to the peripheral transmission electrodes TE1, TE5, TE6, and TE10 via the ground switching devices SW1_G, SW5_G, SW6_G, and SW10 _G that are turned on in the second driving mode.

Figure 8A:
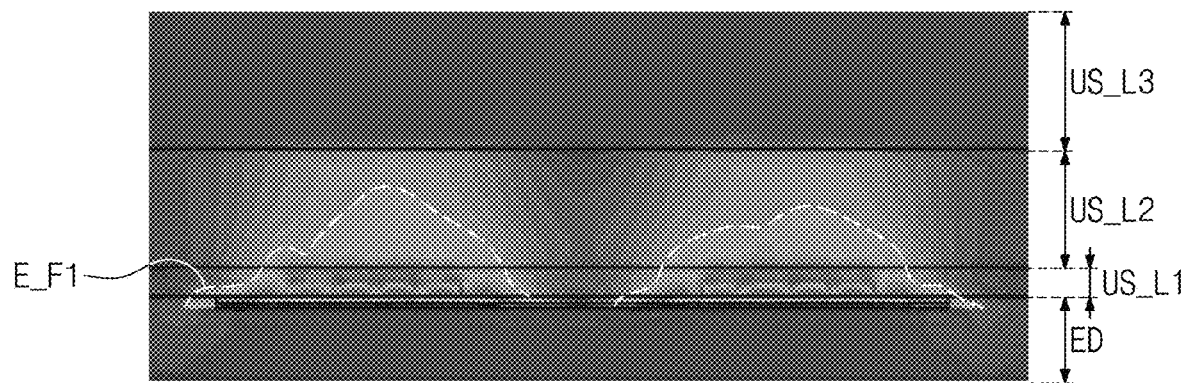
FIG. 8A is a view illustrating an intensity of an electric field when the electronic device shown in FIG. 6A is used.
Figure 8B:
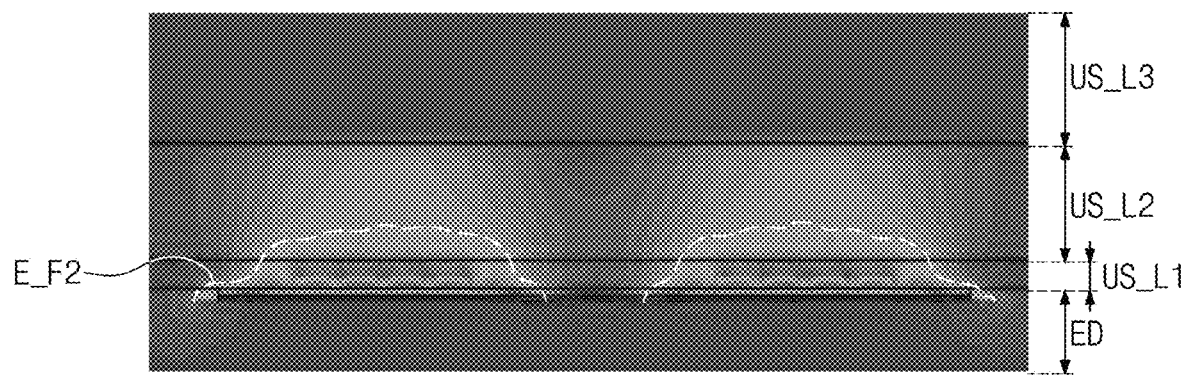
FIG. 8B is a view illustrating an intensity of an electric field when the electronic device shown in FIG. 7A is used.

FIG. 8A is a view showing an intensity of an electric field when the electronic device shown in FIG. 6A is used, and FIG. 8B is a view showing an intensity of an electric field when the electronic device shown in FIG. 7A is used.

Referring to FIG. 8A, when the peripheral transmission electrodes TE1, TE5, TE6, and TE10 are in the floating state, an electric field formed between the transmission sensing electrode Tx_V and the reception sensing electrode Rx_V is defined as a first electric field E_F1. Referring to FIG. 8B, when the ground voltage $V_{GND}$ (refer to FIG. 7B) is applied to the peripheral transmission electrodes TE1, TE5, TE6, and TE10, an electric field formed between the transmission sensing electrode Tx_V and the reception sensing electrode Rx_V is referred to as a second electric field E F2.

When the ground voltage $V_{GND}$ (refer to FIG. 7B) is applied to the peripheral transmission electrodes TE1, TE5, TE6, and TE10, a depth of penetration of the second electric field E_F2 formed between the transmission sensing electrode Tx_V and the reception sensing electrode Rx_V may decrease by a fringe field. For example, when the peripheral transmission electrodes TE1, TE5, TE6, and TE10 are in the floating state, a depth of penetration of the first electric field E_F1 formed between the transmission sensing electrode Tx_V and the reception sensing electrode Rx_V may be greater than that of the second electric field E_F2. The state of the peripheral transmission electrodes TE1, TE5, TE6, and TE10 should not be limited to any one particular state and may be set according to the intensity and the depth of penetration of the electric field formed between the transmission sensing electrode Tx_V and the reception sensing electrode Rx_V.

Figure 9A:
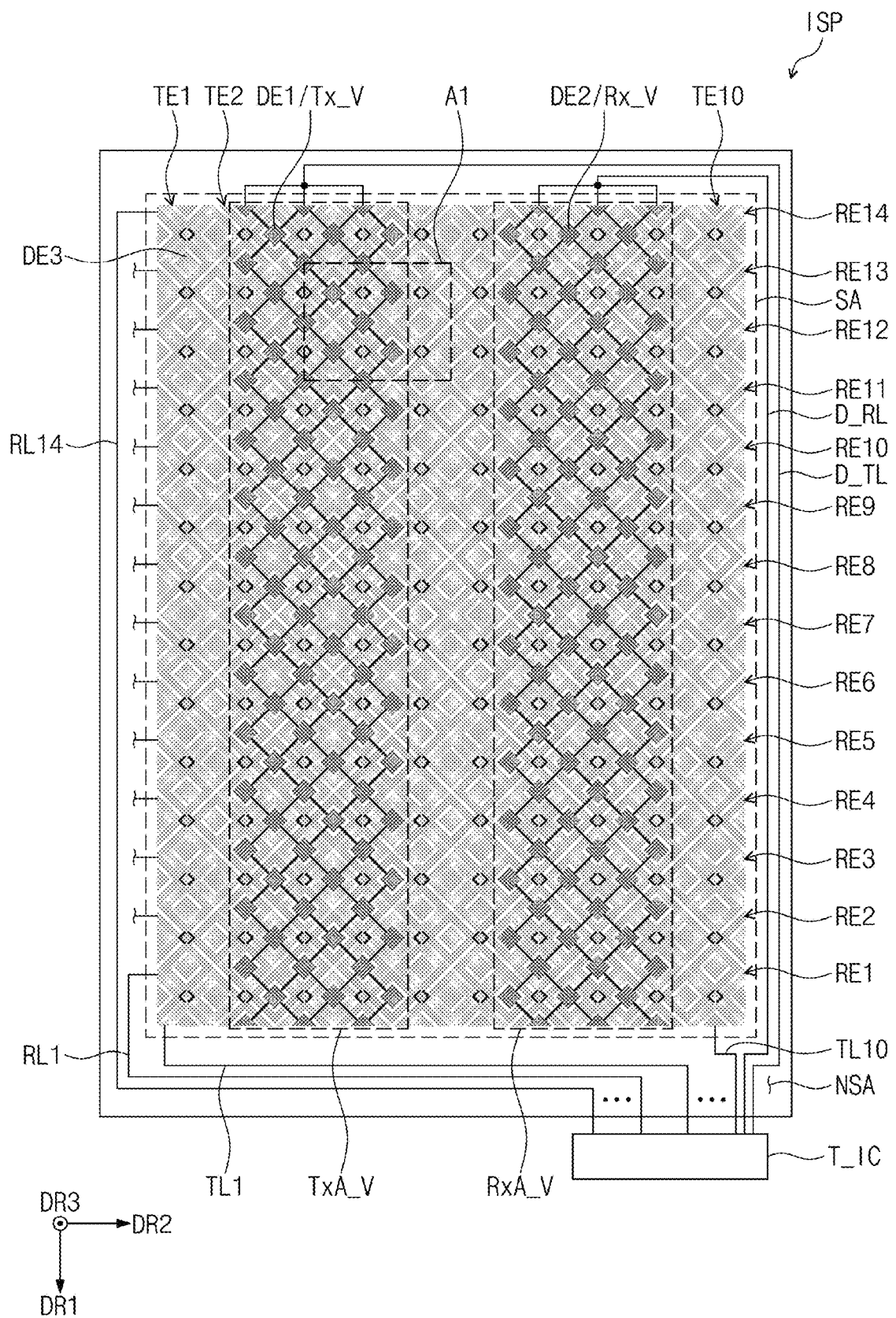
FIG. 9A is a plan view of another embodiment of the input sensor of FIG. 1B illustrating an operation thereof in a second driving mode.
Figure 9B:
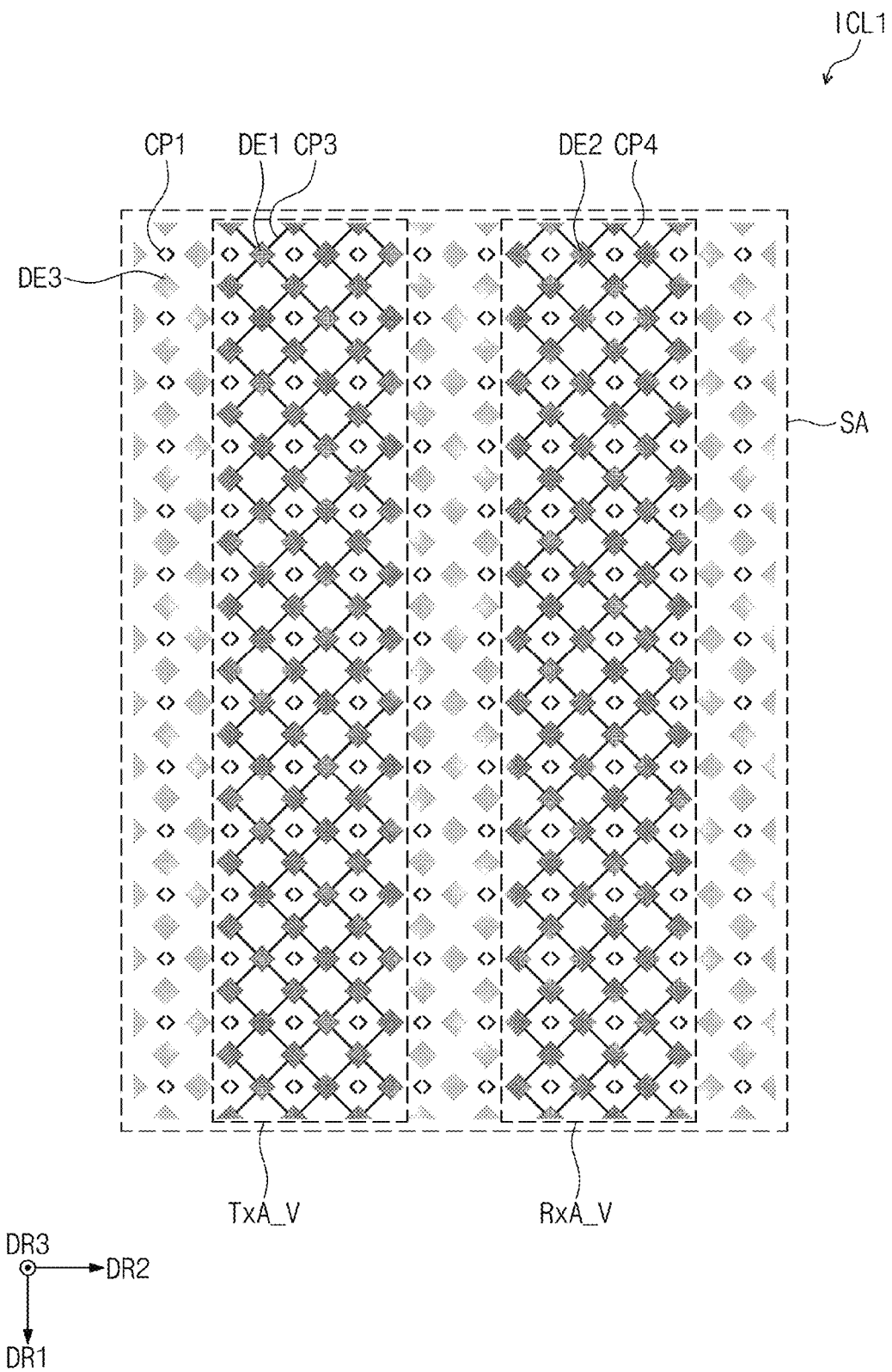
FIG. 9B is a plan view illustrating a first conductive layer shown in FIG. 9A.
Figure 9C:
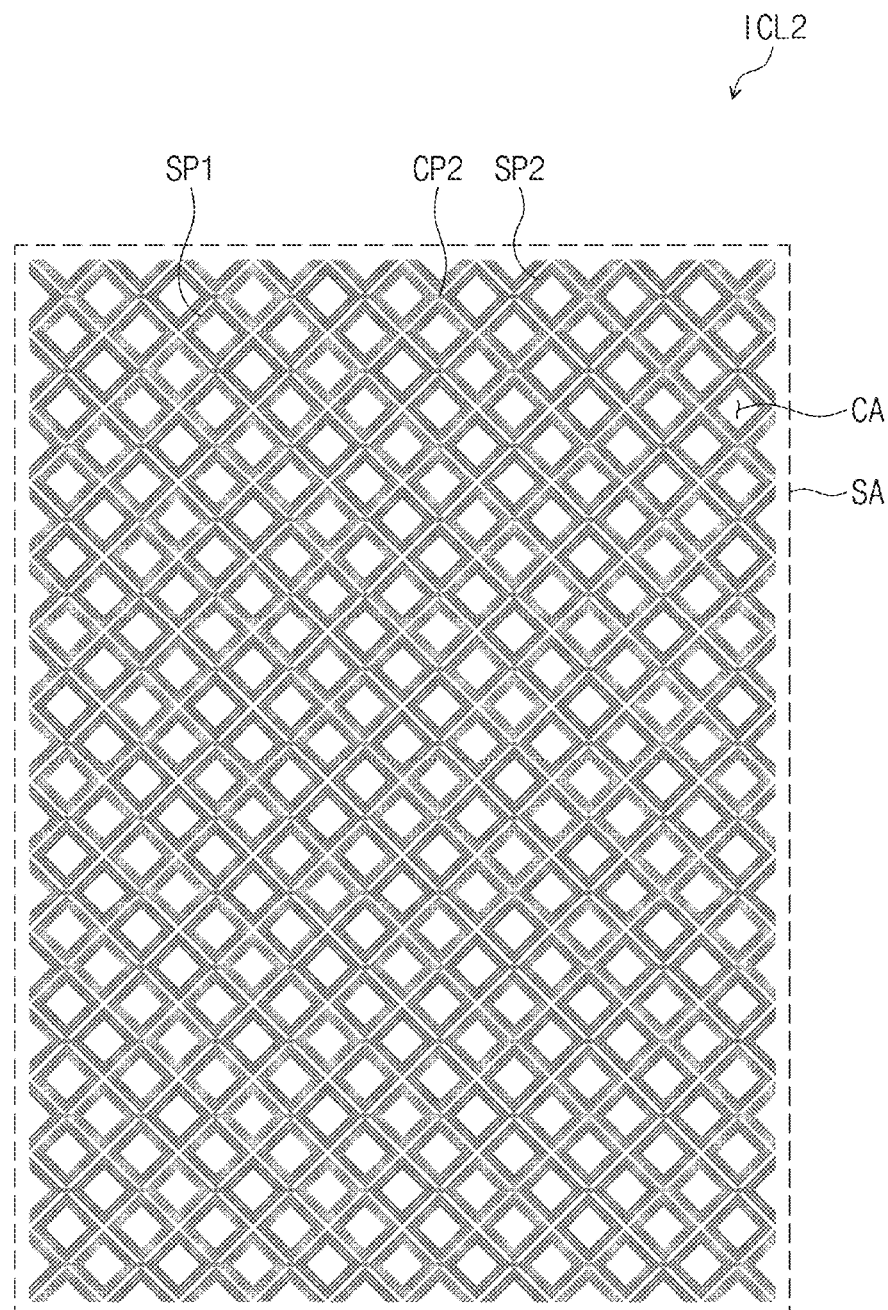
FIG. 9C is a plan view illustrating a second conductive layer shown in FIG. 9A.
Figure 9D:
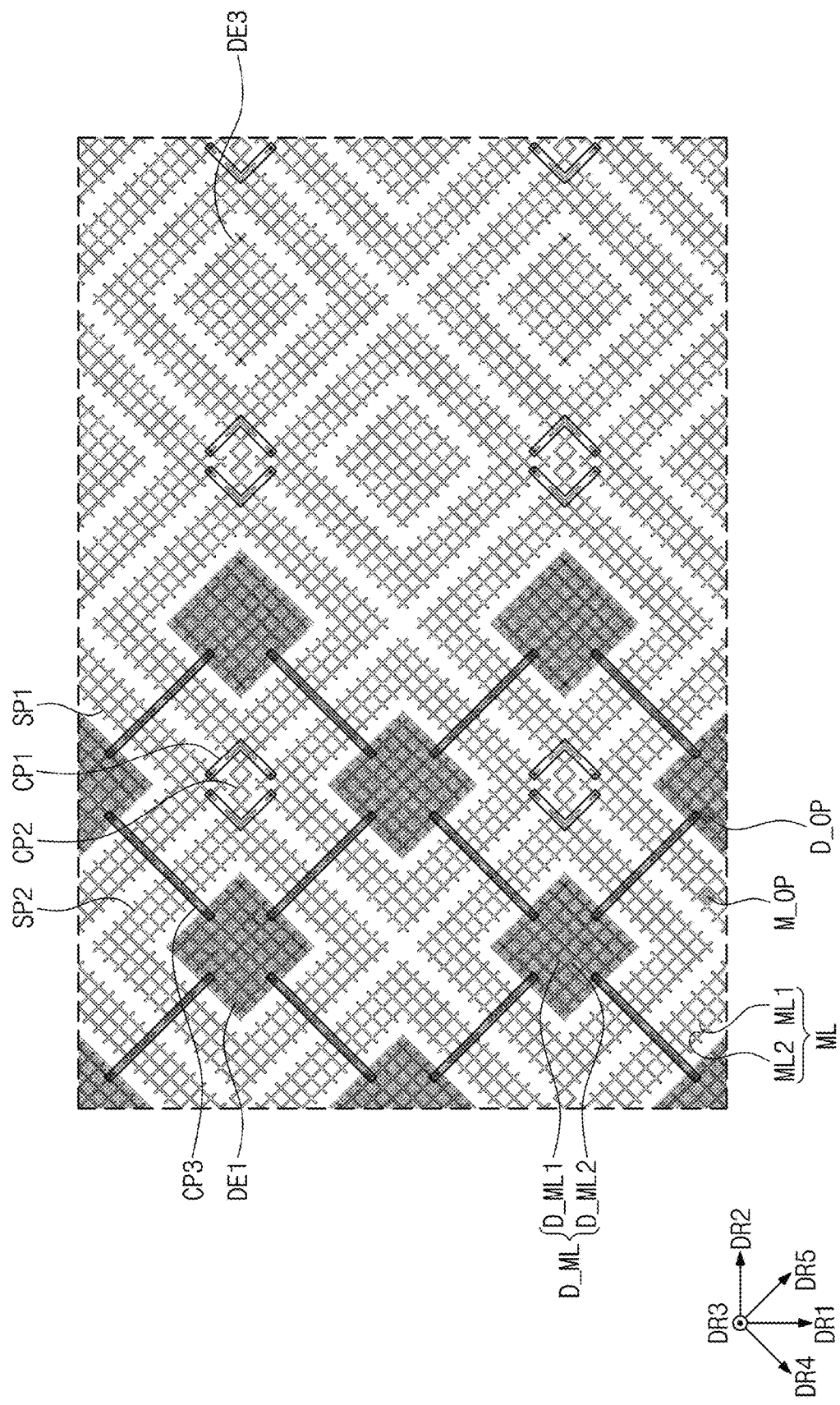
FIG. 9D is an enlarged plan view of an area A1 shown in FIG. 9A.

FIG. 9A is a plan view showing an input sensor ISP operated in a second driving mode, and FIG. 9B is a plan view showing a first conductive layer shown in FIG. 9A. FIG. 9C is a plan view showing a second conductive layer shown in FIG. 9A, and FIG. 9D is an enlarged plan view showing an area A1 shown in FIG. 9A.

Referring to FIGS. 9A, 9B, and 9C, the input sensor ISP may further include a plurality of dummy electrodes DE1, DE2, and DE3. The dummy electrodes DE1, DE2, and DE3 may be disposed to be spaced apart from transmission electrodes TE1 to TE10 and reception electrodes RE1 to RE14. Accordingly, the dummy electrodes DE1, DE2, and DE3 may be electrically separated from the transmission electrodes TE1 to TE10 and the reception electrodes RE1 to RE14.

Each of the dummy electrodes DE1, DE2, and DE3 may be surrounded by at least one of a first sensing part SP1 and a second sensing part SP2 when viewed in a plane. For example, each of the first and second sensing parts SP1 and SP2 may have a lozenge shape, and an empty space CA may be defined at a center area of the lozenge shape. In this case, the dummy electrodes DE1, DE2, and DE3 may be disposed in the empty space CA and may be electrically separated from the first and second sensing parts SP1 and SP2. In a first driving mode, the dummy electrodes DE1, DE2, and DE3 may be in a floating state. Accordingly, the dummy electrodes DE1, DE2, and DE3 may prevent a parasitic capacitance from being generated between the transmission electrodes TE1 to TE10 and the reception electrodes RE1 to RE14 and the electrodes included in the light emitting element OLED (refer to FIG. 4) in the first driving mode.

The input sensor ISP may measure the body composition of the user in the second driving mode using the dummy electrodes DE1, DE2, and DE3. In detail, first dummy electrodes DE1 among the dummy electrodes DE1, DE2, and DE3 may be used as a transmission sensing electrode Tx_V, and second dummy electrodes DE2 among the dummy electrodes DE1, DE2, and DE3 may be used as a reception sensing electrode Rx_V.

The input sensor ISP may further include a dummy transmission line D_TL and a dummy reception line D_RL. The dummy transmission line D_TL and the dummy reception line D_RL may be disposed in a non-sensing area NSA. The dummy transmission line D_TL may be electrically connected to one side of the transmission sensing electrode Tx_V, and the dummy reception line D_RL may be electrically connected to one side of the reception sensing electrode Rx_V. However, embodiments are not limited thereto or thereby. As an example, the input sensor ISP may further include a dummy transmission line electrically connected to the other side of the transmission sensing electrode Tx_V.

The transmission sensing electrode Tx_V and the reception sensing electrode Rx_V may be electrically connected to the sensor controller T_IC via the dummy transmission line D_TL and the dummy reception line D_RL. The sensor controller T_IC may output a transmission signal in the second driving mode, may apply the transmission signal to the dummy transmission line D_TL, and may receive a reception signal from the dummy reception line D_RL. In the second driving mode, third dummy electrodes DE3 may be in the floating state.

As shown in FIGS. 9A and 9B, a first vertical sensing area TxA_V and a second vertical sensing area RxA_V may be defined in the input sensor ISP. Each of the first vertical sensing area TxA_V and the second vertical sensing area RxA_V may extend in the first direction DR1, and the first vertical sensing area TxA_V and the second vertical sensing area RxA_V may be disposed to be spaced apart from each other in the second direction DR2. The first dummy electrodes DE1 may be disposed in the first vertical sensing area TxA_V, and the second dummy electrodes DE2 may be disposed in the second vertical sensing area RxA_V.

The first dummy electrodes DE1 may be electrically connected to each other, and the second dummy electrodes DE2 may be electrically connected to each other. The first dummy electrodes DE1 may be electrically connected to each other via a third connection part CP3, and the second dummy electrodes DE2 may be electrically connected to each other via a fourth connection part CP4. As an example, the first dummy electrodes DE1 may be integrally formed with the third connection part CP3, and the second dummy electrodes DE2 may be integrally formed with the fourth connection part CP4. For example, the first dummy electrodes DE1 and the third connection part CP3 may be formed of the same material, and the second dummy electrodes DE2 and the fourth connection part CP4 may be formed of the same material.

As shown in FIG. 9B, a first conductive layer ICL1 may include the dummy electrodes DE1, DE2, and DE3, first connection parts CP1, and the third and fourth connection parts CP3 and CP4. As shown in FIG. 9C, a second conductive layer ICL2 may include first sensing parts SP1, second sensing parts SP2, and second connection parts CP2. For example, the dummy electrodes DE1, DE2, and DE3 may be disposed on a layer different from a layer on which the first and second sensing parts SP1 and SP2 are disposed. In addition, each of the dummy electrodes DE1, DE2, and DE3 may be disposed corresponding to the empty space CA defined in the center area of each of the first and second sensing parts SP1 and SP2.

Referring to FIG. 9D, each of the first sensing parts SP1 and the second sensing parts SP2 may include a plurality of mesh lines ML. The mesh lines ML may include a first mesh line ML1 extending in a fourth direction DR4 and a second mesh line ML2 extending in a fifth direction DR5 and crossing the first mesh line ML1. The fourth direction DR4 is a direction inclined with respect to the first and second directions DR1 and DR2, and the fifth direction DR5 is a direction intersecting the fourth direction DR4 and inclined with respect to the first and second directions DR1 and DR2. The first mesh line ML1 and the second mesh line ML2 cross each other to define mesh openings M_OP.

Each of the dummy electrodes DE1, DE2, and DE3 may include a plurality of dummy mesh lines D_ML. The dummy mesh lines D_ML may include a first dummy mesh line D_ML1 extending in the fourth direction DR4 and a second dummy mesh line D_ML2 extending in the fifth direction R5 and crossing the first dummy mesh line D_ML1. The first dummy mesh line D_ML1 and the second dummy mesh line D_ML2 may cross each other to define dummy mesh openings D_OP.

The mesh openings M_OP and the dummy mesh openings D_OP may overlap the light emitting areas PXA (refer to FIG. 2C) to which the light generated by the light emitting element OLED (refer to FIG. 2C) is provided when viewed in a plane. Accordingly, the light exiting from the display panel DP (refer to FIG. 2C) may be provided to the window WM (refer io to FIG. 2C) without interfering with the mesh lines ML.

The input sensor ISP may obtain the information on the body composition of the user US based on the variation of mutual capacitance between the transmission sensing electrode Tx_V and the reception sensing electrode Rx_V in the vertical measuring mode. When the input sensor ISP is operated in the second driving mode, the electric field E_F (refer to FIG. 5) may be formed between the transmission sensing electrode Tx_V and the reception sensing electrode Rx_V. An operational principle of the input sensor ISP and the sensor controller T_IC in the second driving mode may be similar to the operational principle described with reference to FIGS. 4A to 7B. Therefore, descriptions of the operational principle of the input sensor ISP and the sensor controller T_IC are omitted in order to avoid redundancy.

Figure 10:
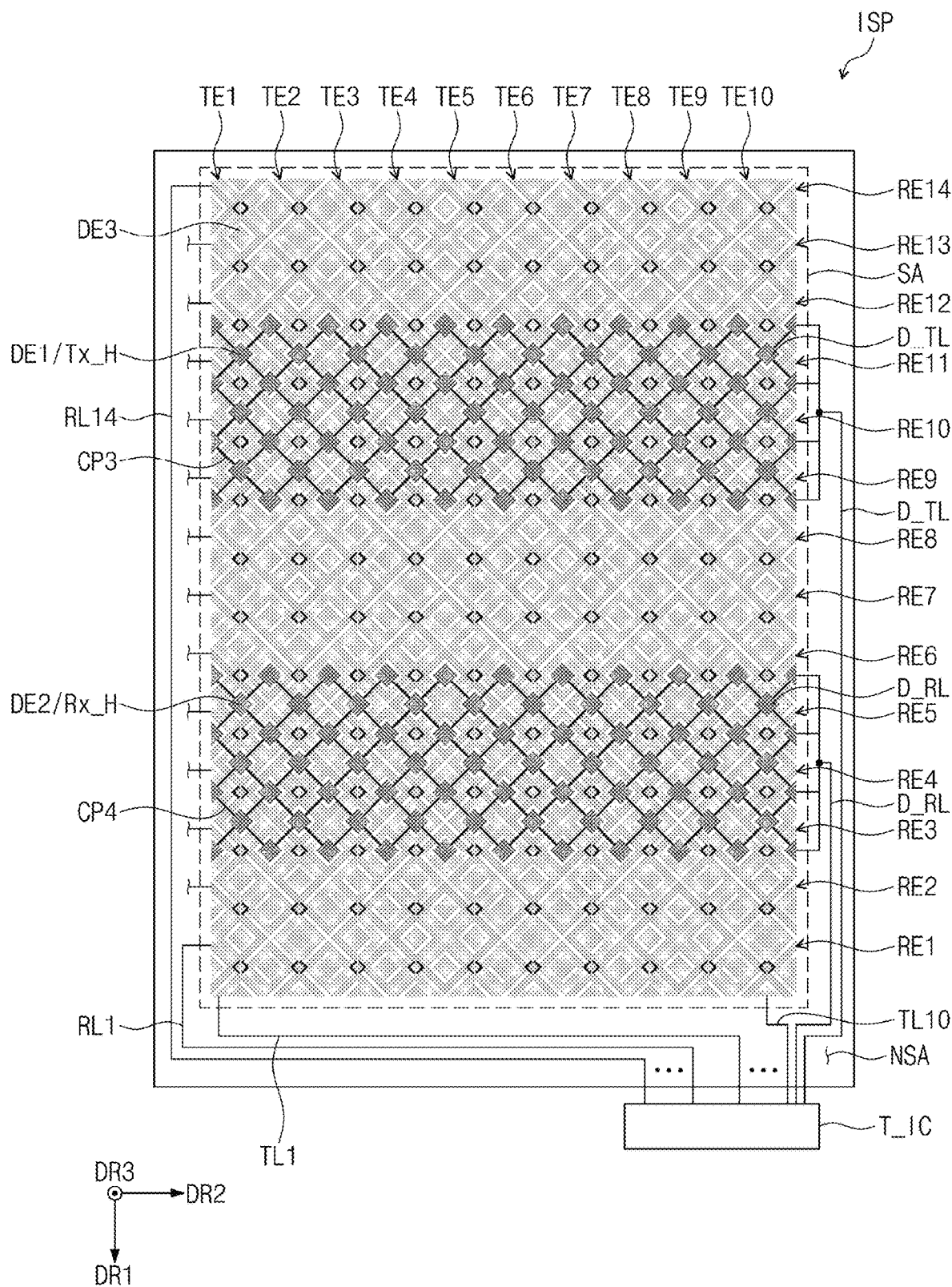
FIG. 10 is a plan view of the input sensor of FIG. 9A illustrating an operation thereof in a second driving mode.

FIG. 10 is a plan view showing an input sensor ISP operated in a second driving mode.

Referring to FIG. 10, the input sensor ISP may further include a plurality of dummy electrodes DE1, DE2, and DE3. The dummy electrodes DE1, DE2, and DE3 may be disposed to be spaced apart from transmission electrodes TE1 to TE10 and reception electrodes RE1 to RE14. Accordingly, the dummy electrodes DE1, DE2, and DE3 may be electrically separated from the transmission electrodes TE1 to TE10 and the reception electrodes RE1 to RE14.

The input sensor ISP may measure the body composition of the user using the dummy electrodes DE1, DE2, and DE3 in the second driving mode. In detail, first dummy electrodes DE1 among the dummy electrodes DE1, DE2, and DE3 may be used as a transmission sensing electrode Tx_H, and second dummy electrodes DE2 among the dummy electrodes DE1, DE2, and DE3 may be used as a reception sensing electrode Rx_H.

In particular, as shown in FIG. 10, a first horizontal sensing area TxA_H and a second horizontal sensing area RxA_H may be defined in the input sensor ISP. Each of the first horizontal sensing area TxA_H and the second horizontal sensing area RxA_H may extend in the second direction DR2, and the first horizontal sensing area TxA_H and the second horizontal sensing area RxA_H may be disposed to be spaced apart from each other in the first is direction DR1. The first dummy electrodes DE1 may be disposed in the first horizontal sensing area TxA_H, and the second dummy electrodes DE2 may be disposed in the second horizontal sensing area RxA_H.

The first dummy electrodes DE1 may be electrically connected to each other, and the second dummy electrodes DE2 may be electrically connected to each other. The first dummy electrodes DE1 may be electrically connected to each other via a third connection part CP3, and the second dummy electrodes DE2 may be electrically connected to each other via a fourth connection part CP4. As an example, the first dummy electrodes DE1 may be integrally formed with the third connection part CP3, and the second dummy electrodes DE2 may be integrally formed with the fourth connection part CP4. For example, the first dummy electrodes DE1 and the third connection part CP3 may be formed of the same material, and the second dummy electrodes DE2 and the fourth connection part CP4 may be formed of the same material.

The input sensor ISP may obtain the information on the body composition of the user US based on the variation of mutual capacitance between the transmission sensing electrode Tx_H and the reception sensing electrode Rx_H in the horizontal measuring mode. When the input sensor ISP is operated in the second driving mode, the electric field E_F (refer to FIG. 5) may be formed between the transmission sensing electrode Tx_H and the reception sensing electrode Rx_H. An operational principle of the input sensor ISP and the sensor controller T_IC in the second driving mode may be similar to the operational principle described with reference to FIGS. 4A to 7B. Accordingly, descriptions of the operational principle of the input sensor ISP and the sensor controller T_IC are omitted in order to avoid redundancy.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. An electronic device comprising:
a display panel configured to display an image;
an input sensor disposed on the display panel and comprising first electrodes, second electrodes electrically insulated from the first electrodes, and dummy electrodes electrically insulated from the first electrodes and the second electrodes; and
a sensor controller electrically connected to the input sensor, the sensor controller configured to drive the input sensor in a first driving mode or a second driving mode, wherein:
in the first driving mode, the sensor controller is configured to measure a variation of capacitance between the first electrodes and the second electrodes to generate location information of an input, and
in the second driving mode, the sensor controller is configured to use a first group among the dummy electrodes as a transmission sensing electrode and to use a second group among the dummy electrodes as a reception sensing electrode to analyze a body composition.

2. The electronic device of claim 1, wherein:
in the first driving mode, the dummy electrodes are in a floating state,
in the second driving mode, the first group among the dummy electrodes is configured to receive transmission sensing signals from the sensor controller, and
in the second driving mode, the second group among the dummy electrodes is configured to transmit reception sensing signals to the sensor controller.

3. The electronic device of claim 1, wherein each of the first electrodes and the second electrodes comprises a sensing part through which a center portion is opened, and each of the dummy electrodes is disposed to overlap the center portion of the sensing part.

4. The electronic device of claim 3, wherein the dummy electrodes of the first group among the dummy electrodes are electrically connected to each other, and the dummy electrodes of the second group among the dummy electrodes are electrically connected to each other.

5. The electronic device of claim 4, wherein the input sensor further comprises:
a first dummy connection part electrically connecting the dummy electrodes of the first group; and
second dummy connection part electrically connecting the dummy electrodes of the second group.

6. The electronic device of claim 1, wherein:
the first electrodes comprise transmission electrodes, and the second electrodes comprise reception electrodes, and wherein:
the transmission electrodes extend in a first direction, and are arranged in a second direction intersecting the first direction, and
the reception electrodes extend in the second direction, and are arranged in the first direction.

7. The electronic device of claim 6, wherein the transmission sensing electrode is disposed to be spaced apart from the reception sensing electrode in the second direction.

8. The electronic device of claim 1, wherein:
the first electrodes comprise reception electrodes, and the second electrodes comprise transmission electrodes, and wherein:
the reception electrodes extend in a second direction, and are arranged in a first direction intersecting the second direction, and the transmission electrodes extend in the first direction, and are arranged in the second direction.

9. The electronic device of claim 8, wherein the transmission sensing electrode is disposed to be spaced apart from the reception sensing electrode in the first direction.

10. The electronic device of claim 1, wherein the display panel comprises:
   a display element layer comprising a light emitting element; and
   an encapsulation layer disposed on the display element layer.

11. The electronic device of claim 10, wherein the input sensor is disposed directly on the encapsulation layer.

12. The electronic device of claim 1, further comprising an adhesive film disposed between the display panel and the input sensor.

* * * * *